(12) United States Patent
Carroll et al.

(10) Patent No.: US 8,501,233 B2
(45) Date of Patent: Aug. 6, 2013

(54) COMPOSITIONS AND METHODS FOR TREATING CANCER

(75) Inventors: David Loren Carroll, Winston-Salem, NC (US); John H. Stewart, IV, Clemmons, NC (US); Nicole H. Levi, Winston-Salem, NC (US)

(73) Assignees: Wake Forest University, Winston Salem, NC (US); Wake Forest University Health Sciences, Winston Salem, NC (US)

( * ) Notice: Subject to any disclaimer, the term of this patent is extended or adjusted under 35 U.S.C. 154(b) by 501 days.

(21) Appl. No.: 12/530,852

(22) PCT Filed: Mar. 13, 2008

(86) PCT No.: PCT/US2008/003332
§ 371 (c)(1),
(2), (4) Date: Apr. 22, 2010

(87) PCT Pub. No.: WO2008/112277
PCT Pub. Date: Sep. 18, 2008

(65) Prior Publication Data
US 2010/0209479 A1    Aug. 19, 2010

Related U.S. Application Data

(60) Provisional application No. 60/906,746, filed on Mar. 13, 2007.

(51) Int. Cl.
*A61K 41/00* (2006.01)
*A61K 9/14* (2006.01)
*A61K 9/51* (2006.01)
*A61K 9/00* (2006.01)
*A61N 1/40* (2006.01)

(52) U.S. Cl.
CPC ......... *A61K 41/0052* (2013.01); *A61K 9/0092* (2013.01); *A61K 9/14* (2013.01); *A61K 9/51* (2013.01); *A61N 1/406* (2013.01); *Y10S 977/742* (2013.01); *Y10S 977/743* (2013.01); *Y10S 977/752* (2013.01); *Y10S 977/906* (2013.01); *Y10S 977/911* (2013.01)
USPC ......... 424/489; 514/492; 977/742; 977/743; 977/752; 977/906; 977/911; 977/742

(58) Field of Classification Search
None
See application file for complete search history.

(56) References Cited

U.S. PATENT DOCUMENTS

| 5,554,638 | A * | 9/1996 | Dewhirst et al. | 514/398 |
| 6,200,309 | B1 * | 3/2001 | Rice et al. | 606/10 |
| 2002/0103517 | A1 * | 8/2002 | West et al. | 607/88 |
| 2003/0180491 | A1 * | 9/2003 | Hirsch et al. | 428/35.7 |
| 2005/0152891 | A1 * | 7/2005 | Toone et al. | 424/125 |
| 2006/0014157 | A1 * | 1/2006 | Kawabe et al. | 435/6 |
| 2006/0051290 | A1 | 3/2006 | Wilson et al. | |

FOREIGN PATENT DOCUMENTS

| JP | 2005075720 A | 3/2005 |
| KR | 2006016601 A | 2/2006 |
| WO | 03084869 A | 10/2003 |
| WO | 2005097672 A | 10/2005 |
| WO | 2006099445 A | 9/2006 |

OTHER PUBLICATIONS

NWS Kam, M O'Connell, JA Wisdom, H Dai. "Carbon nanotubes as multifunctional biological transporters and near-infrared agents for selective cancer cell destruction." Proceedings of the National Academy of Sciences, vol. 102, No. 33, Aug. 16, 2005, pp. 11600-11605.*
SK Huang, PR Stauffer, K Hong, JWH Guo, TL Phillips, A Huang, D Papahadjopoulos. "Liposomes and Hyperthermia in Mice: Increased Tumor Uptake and Therapeutic Efficacy of Doxorubicin in Sterically Stabilized Liposomes." Cancer Research, vol. 54, Apr. 15, 1994, pp. 2186-2191.*
EG Matyakin, AA Uvarov. "Oropharyngeal Region Cancer—Modern Problems of Diagnosis, Treatment and Prognosis." Oncology Reviews, Sovient Medical Reviews / Section F. vol. 4, Part 2, Jan. 1, 1991. pp. 24 and 25 included, along with the cover page and an additional page (4 total pages included).*
AG van der Heijden, CFJ Jansen, G Verhaegh, MA O'Donnell, JA Schalken, JA Witjes. The Effect of Hyperthermia on Mitomycin-C Induced Cytotoxicity in Four Human Bladder Cancer Cell Lines. European Urology, vol. 46, 2004, pp. 670-674.*
International Search Report mailed on Nov. 15, 2007 in International Application No. PCT/US2007/012492.
Clare Sansom, Nanotechnology used to kill tumour cells, Lancet Oncology, Sep. 2005, p. 641, vol. 6, No. 9, Lancet Publishing Group, London, GB.
Nadine Wong Shi Kam et al, Carbon nanotubes as multifunctional biological transporters and near-infrared agents for selective cancer destruction, Proceedings of the National Academy of Sciences of USA, Aug. 16, 2005, pp. 11600-11605, vol. 102, No. 33, National Academy of Science, Washington, DC.
Zhu Yinghuai et al, Substituted Carborane-Appended Water Soluable Single-Wall Carbon Nanotubes: New Approach to Boron Neutron Capture Therapy Drug Delivery, Journal of the American Chemical Society, Jun. 16, 2005, pp. 9875-9880, vol. 127, American Chemical Society.
International Search Report mailed on Sep. 29, 2008 in International Application No. PCT/US2008/003332.
T. M. Whitney et al, Fabrication and Magnetic Properties of Arrays of Metallic Nanowires, Science, Sep. 3, 1993, vol. 261, pp. 1315-1319, American Association for the Advancement of Science.

* cited by examiner

*Primary Examiner* — Frederick Krass
*Assistant Examiner* — Isaac Shomer
(74) *Attorney, Agent, or Firm* — J. Clinton Wimbish; Smith Moore Leatherwood LLP

(57) ABSTRACT

The present invention relates to compositions and methods for treating cancer and, in particular, to composition and methods comprising nanostructures. In one embodiment, the present invention provides a composition comprising a mixture, the mixture comprising at least one nanoparticle and at least one chemotherapeutic.

27 Claims, 9 Drawing Sheets

COMPOSITIONS AND METHODS FOR TREATING CANCER

RELATED APPLICATION DATA

The present application claims priority under 35 U.S.C §119(e) to U.S. Provisional Patent Application Ser. No. 60/906,746 filed Mar. 13, 2007.

STATEMENT OF GOVERNMENT LICENSE RIGHTS

This invention was made through the support of the Department of Defense—United States Air Force Office of Scientific Research (AFOSR) Grant No. FA9550-04-1-0161. The Federal Government may retain certain license rights in this invention.

FIELD OF THE INVENTION

The present invention relates to compositions and methods for treating cancer and, in particular, to compositions and methods comprising nanostructures.

BACKGROUND OF THE INVENTION

Cancer is responsible for one out of every four deaths in the United States. About 1.4 million people are expected to be diagnosed with cancer in 2007. Of that number, more than 550,000 are expected to die of the disease.

Many strategies for the treatment of cancer currently exist, such as radiation therapy, chemotherapy, and surgery including the complete removal of cancerous tissue as well as cytoreduction and palliation. In a number of cases, cancer treatment strategies comprise adjuvant therapies such as surgery and chemotherapy. In cytoreductive procedures, for example, any abnormal tissue remaining after the surgery can be treated with chemotherapy.

The inherently destructive nature of cancer therapies often results in harmful side-effects such as damage to healthy, non-cancerous tissues. The cytotoxicity of chemotherapeutic agents, for example, can result in anemia, alopecia (hair loss), nausea and vomiting, damage to nerves leading to burning, numbness, tingling or shooting pain. Chemotherapy can additionally precipitate immunosuppresion and myelosupression thereby increasing a patient's chances for infection and other disease.

The efficacy of some chemotherapeutic agents can be enhanced by heating or inducing hyperthermia in the cancerous tissue being treated. Generating and maintaining a constant elevated temperature over a large area of the body, such as the peritoneal cavity, however, is difficult and time consuming. Moreover, maintaining an elevated temperature over a large area of the body can affect and potentially damage non-cancerous tissues and organs.

SUMMARY

In view of the foregoing problems, the present invention provides compositions and methods which can assist in reducing the toxicity of chemotherapeutic agents to healthy tissues while maintaining their efficacy in killing cancerous tissues. Moreover, compositions and methods of the present invention can be useful in administering hyperthermic chemotherapies such as, but not limited to, intraperitoneal hyperthermic chemoperfusion. The present invention, in some embodiments, provides compositions and methods comprising nanostructures for the treatment of cancer.

In one embodiment, the present invention provides a mixture comprising at least one nanoparticle and at least one chemotherapeutic agent. In some embodiments, at least one nanoparticle comprises a plurality of nanoparticles. In some embodiments, at least one chemotherapeutic agent comprises a plurality of chemotherapeutic agents. In some embodiments, the mixture further comprises a physiologically acceptable carrier.

In another embodiment, the present invention provides a composition comprising at least one nanoparticle and at least one chemotherapeutic agent at least partially disposed in the nanoparticle. In some embodiments, the chemotherapeutic agent is fully disposed within the nanoparticle. In some embodiments, at least one nanoparticle comprises a plurality of nanoparticles. At least one chemotherapeutic agent, in some embodiments, comprises a plurality of chemotherapeutic agents.

Nanoparticles suitable for use in compositions of the present invention, according to some embodiments, comprise carbon nanoparticles. Carbon nanoparticles, in some embodiments, comprise carbon nanotubes, including single-walled carbon nanotubes (SWNT), multi-walled carbon nanotubes (MWNT) or combinations thereof. In other embodiments, nanoparticles comprise inorganic nanoparticles such as a nanoshells, nanowires, nanotubes, or combinations thereof. Inorganic nanotubes, in some embodiments, comprise transition metals, metal oxides, and boron nitrides.

In some embodiments of compositions of the present invention, a surface of at least one nanoparticle is functionalized. In one embodiment, for example, a surface of a carbon nanotube is functionalized with at least one hydrophilic chemical species. Hydrophilic chemical species suitable for functionalizing surfaces of carbon nanotubes and/or other nanoparticles described herein, in some embodiments, comprise species having carboxyl groups. In other embodiments, suitable hydrophilic chemical species comprise hydrophilic polymers such as poly(dimethyldiallylammonium chloride) (PDDA), polyethylene glycol, alkoxylated polyethylene glycol, polypropylene glycol, polyvinyl pyrrolidone, polyvinyl alcohol, polystyrene sulfonate, or poly($\epsilon$-caprolactone) or combinations thereof. In some embodiments, hydrophilic polymers comprise ethylene oxide-propylene oxide copolymers, including block copolymers.

In some embodiments, surfaces of carbon nanotubes and/or other nanoparticles described herein are functionalized with radioactive labels, such as $^{111}$In, chelating agents, such as diethylentriaminepentaacetic acid (DTPA), and/or enzymes, such as soybean peroxidase and alpha chymotrypsin. In other embodiments, surfaces of carbon nanotubes and/or other nanoparticles are functionalized with ammonium, bovine serum albumin, schizophyllan, congo red dye; amylopectin, galactose, chitosan, or combinations thereof. In a further embodiment, surfaces of carbon nanotubes are and/or other nanoparticles described herein are functionalized with DNA, such as ssDNA, amino acids, dextran, other carbohydrates, or combinations thereof.

In some embodiments, surfaces of nanoparticles, including carbon nanotubes, are functionalized by covalently linking a hydrophilic chemical species to the surface. In other embodiments, surfaces of nanoparticles are functionalized by forming non-covalent intermolecular interactions with a hydrophilic chemical species, including ionic, dipole-dipole, and/or Van der Waals interactions. In a further embodiment, surfaces of nanoparticles described herein are functionalized by forming covalent and non-covalent interactions with one or more hydrophilic chemical species. Functionalization of nanoparticles with hydrophilic chemical species, in some embodiments, increases the solubility and dispersion of the nanoparticles in polar media, such as aqueous solutions.

In other embodiments, a surface of at least one nanoparticle is functionalized with at least one targeting ligand. "Targeting ligand," as used herein, refers to a ligand or receptor having a specific affinity for a particular chemical species. Moreover, "targeting," as used herein, encompasses the use of antibody-antigen binding, ligand-receptor binding, and other chemical binding interactions. In some embodiments, targeting ligands comprise polyclonal antibodies, monoclonal antibodies, chimeric antibodies, humanized antibodies, recombinant antibodies, bispecific antibodies, antibody fragments, recombinant single chain antibody fragments, aptamers, ssDNA fragments, and peptides.

Targeting ligands, according to some embodiments of the present invention, are operable to bind to a cancer marker. In such embodiments, a targeting ligand can be designed to target a specific cancer cell marker or markers. The particular cancer cell marker may be specific to, but not limited to, the type and location of the cancer, such as, for example, tumors, metastatic cancer, minimal residual disease and the like.

The cancer marker or markers may be selected such that they represent a viable target on the cancer cell of interest, such as colorectal cancer cells. Cancer markers, in some embodiments, may be expressed on the surface of cancer cells and not expressed on the surface of healthy cells to permit adequate cellular differentiation. In some embodiments, cancer markers are not readily shed from cellular surfaces. In the event that a cancer marker is shed, according to some embodiments, a targeting ligand may still recognize a particular epitope of the marker that remains on the cellular surface. Alternatively, if a cancer marker is shed, the surface of a nanotube may comprise one or more additional targeting ligands operable to recognize such shed entities as markers for the cancerous cell.

In another aspect, the present invention provides methods of producing compositions for the treatment of cancer as well as methods of using such compositions in the treatment of cancer. In one embodiment, a method of producing a composition for the treatment of cancer comprises providing at least one nanoparticle, providing at least one chemotherapeutic agent, and mixing the at least one nanoparticle and the at least one chemotherapeutic agent. In some embodiments, the at least one nanoparticle and the at least one chemotherapeutic can be mixed in a physiologically acceptable carrier.

In another embodiment, a method for producing a composition comprises providing at least one nanoparticle, providing at least one chemotherapeutic agent, and at least partially disposing the at least one chemotherapeutic agent in the nanoparticle. In some embodiments, the at least one chemotherapeutic agent is fully disposed in the nanoparticle.

In another embodiment, a method of treating cancer comprises providing a composition comprising at least one chemotherapeutic agent and at least one nanoparticle, disposing the composition in contact with cancerous tissue, and accelerating or enhancing the uptake of the at least one chemotherapeutic agent by the cancerous tissue, wherein accelerating or enhancing the uptake comprises heating the cancerous tissue with the at least one nanoparticle. In some embodiments, the chemotherapeutic agent is at least partially disposed in the nanoparticle. In other embodiments, the chemotherapeutic agent is fully disposed within the nanoparticle. In a further embodiment, the chemotherapeutic agent is mixed with the nanoparticle. In some embodiments of methods of the present invention, at least one nanoparticle comprises a plurality of nanoparticles. Additionally, in some embodiments, at least one chemotherapeutic agent comprises a plurality of chemotherapeutic agents.

In some embodiments, disposing the composition in contact cancerous tissue comprises injecting the composition in the cancerous tissue. In other embodiments, disposing the composition in contact with the cancerous tissue comprises administering the composition intravenously, intra-arterially, orally, or topically. In some embodiments, the cancerous tissue is subjected to local or regional perfusion with a composition of the present invention. In one embodiment, regional perfusion with a cancer treating composition of the present invention comprises intraperitoneal perfusion. Intraperitoneal hyperthermic chemoperfusion, for example, is employed for the treatment of peritoneal surface dissemination of colorectal cancer, mesothelioma and sarcoma. In other embodiments, regional perfusion techniques with compositions of the present invention comprise isolated limb perfusion for malignant melanoma and sarcoma, pleural perfusion for malignant pleural mesothelioma, pelvic perfusion for locally advanced rectal cancer, and isolated lung perfusion for metastatic sarcoma.

Heating the cancerous tissue with the at least one nanoparticle, according to some embodiments of the present invention, comprises irradiating the at least one nanoparticle. In some embodiments, the at least one nanoparticle is irradiated with ultraviolet radiation, visible radiation, infrared radiation, or combinations thereof. In other embodiments, the at least one nanoparticle is irradiated with radio frequency radiation or microwave radiation. In some embodiments, the at least one nanoparticle is ablated when irradiated. In other embodiments, the at least one nanoparticle is not ablated when irradiated.

In some embodiments, the cancerous tissue is heated to a temperature of at least about 39° C. by irradiating a plurality of nanoparticles. In another embodiment, the cancerous tissue is heated to a temperature of at least about 42° C. by irradiating a plurality of nanoparticles. In a further embodiment, the cancerous tissue is heated to a temperature of at least about 45° C. by irradiating a plurality of nanoparticles. In some embodiments, the cancerous tissue is heated to a temperature greater than about 45° C. or greater than about 52° C. by irradiating a plurality of nanoparticles. The cancerous tissue, in some embodiments, is heated to a temperature less than about 39° C. or to a temperature ranging from about 39° C. to about 42° C. by irradiating a plurality of nanoparticles.

In another aspect, the present invention provides a method for treating cancer comprising providing a composition comprising at least one nanoparticle having at least one chemotherapeutic agent at least partially disposed therein, disposing the composition in contact with cancerous tissue, and releasing the at least one chemotherapeutic from the at least one nanoparticle. In some embodiments, the chemotherapeutic is fully disposed within the nanoparticle.

Releasing at least one chemotherapeutic agent from a nanoparticle, according to some embodiments, comprises heating the nanoparticle, wherein heating comprises irradiating the nanoparticle. A nanoparticle comprising at least one chemotherapeutic agent, in some embodiments, is irradiated with ultraviolet radiation, visible radiation, infrared radiation, or combinations thereof. In other embodiments, a nanoparticle comprising at least one chemotherapeutic agent is irradiated with radio frequency radiation or microwave radiation.

In some embodiments of releasing at least one chemotherapeutic agent, the nanoparticle is not ablated when heated by irradiation. In other embodiments of releasing at least one chemotherapeutic agent, the nanoparticle is ablated when heated by irradiation.

Nanoparticles, according to some embodiments of methods of the present invention, comprise carbon nanoparticles. A carbon nanoparticle, in some embodiments, comprises a carbon nanotube. In other embodiments, nanoparticles comprise inorganic nanoparticles such as nanotubes, nanoshells, nanowires, or combinations thereof. Inorganic nanotubes, in some embodiments, comprise transition metals, metal oxides, and boron nitrides.

In some embodiments of compositions and methods of the present invention, nanoparticles described herein are extracellular and do not enter into the cells of cancerous tissue and/or healthy tissue. In such embodiment, the nanoparticles can remain in the vasculature of the cancerous tissue.

These and other embodiments of the present invention are described in greater detail in the detailed description which follows. These and other objects, features, and advantages of the present invention will become apparent after review of the following detailed description of the disclosed embodiments.

DETAILED DESCRIPTION

Figure 1:
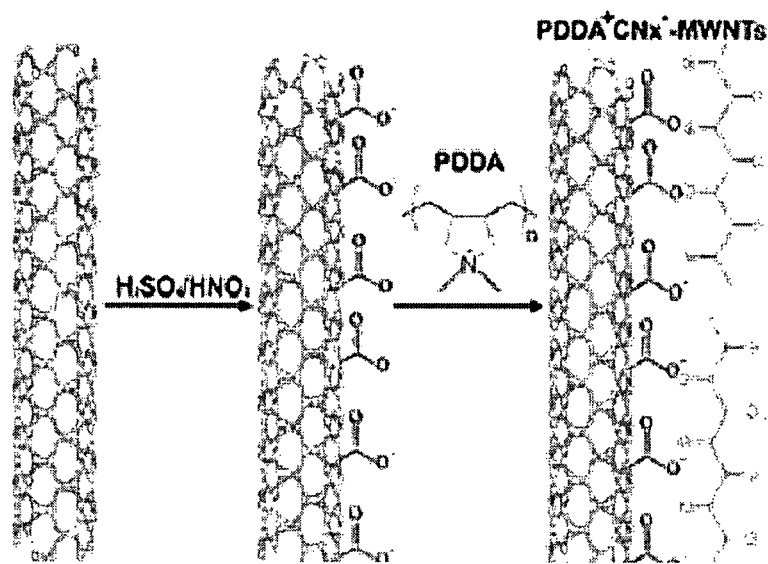
FIG. 1 illustrates a method of functionalizing a surface of a carbon nanotube with hydrophilic chemical species according to an embodiment of the present invention.

The present invention provides compositions and methods for the treatment of cancer. Compositions and methods of the present invention are useful in reducing the toxicity of chemotherapeutic agents to healthy, non-cancerous tissues while maintaining efficacy in killing cancerous tissues. Moreover, compositions and methods of the present invention can find application in hyperthermic chemotherapies, such as intraperitoneal hyperthermic chemoperfusion and others known to one of skill in the art.

In one embodiment, the present invention provides a composition comprising a mixture, the mixture comprising at least one nanoparticle and at least one chemotherapeutic agent. In some embodiments, at least one nanoparticle comprises a plurality of nanoparticles. At least one chemotherapeutic agent, in some embodiments, comprises a plurality of chemotherapeutic agents. In some embodiments, the mixture further comprises a physiological carrier for the at least one nanoparticle and the at least one chemotherapeutic agent.

In another embodiment, the present invention provides a composition comprising at least one nanoparticle and at least one chemotherapeutic agent at least partially disposed in the nanoparticle. In some embodiments, the at least one chemotherapeutic agent is fully disposed within the nanoparticle. At least one nanoparticle, in some embodiments, comprises a plurality of nanoparticles. Moreover, in some embodiments, at least one chemotherapeutic agent comprises a plurality of chemotherapeutic agents.

Turning now to components that can be included in various embodiments of compositions of the present invention, compositions of the present invention comprise at least one nanoparticle. In some embodiments, compositions of the present invention comprise a plurality of nanoparticles. Nanoparticles suitable for use in compositions of the present invention, in some embodiments, comprise carbon nanoparticles. Carbon nanoparticles, according to some embodiments, comprise carbon nanotubes.

In some embodiments, carbon nanotubes comprise single-walled carbon nanotubes (SWNT), multi-walled carbon nanotubes (MWNT), nanohorns, fullerites, or mixtures thereof. Carbon nanotubes, in one embodiment, have a length ranging from about 100 nm to about 3 µm or from about 400 nm to about 1500 nm. In another embodiment, carbon nanotubes have a length ranging from about 500 nm to about 1200 nm, from about 550 nm to about 700 nm, or from about 100 nm to about 350 nm. In a further embodiment, carbon nanotubes have a length ranging from about 700 nm to about 1000 nm. In some embodiments, carbon nanotubes have a length greater than about 1 µm or a length ranging from about 1 µm to about 2 µm. In some embodiments, carbon nanotubes have a length ranging from about 1.5 µm to about 2 µm or from about 2 µm to about 2.5 µm. In one embodiment, carbon nanotubes have a length ranging from about 2.5 µm to about 3 µm or greater than about 3 µm.

In addition to length, carbon nanotubes, in some embodiments, have an internal diameter ranging from about 0.1 nm to about 100 nm. In other embodiments, carbon nanotubes have an internal diameter ranging from about 5 nm to about 75 nm or from about 15 nm to about 60 nm. In a further embodiment, carbon nanotubes have an internal diameter ranging from about 30 nm to about 50 nm.

Carbon nanotubes, according to some embodiments, can be doped with boron, nitrogen, or combinations thereof. In one embodiment, for example, doped carbon nanotubes comprise boron in amount ranging from about 0.01 weight percent to about 10 weight percent. In another embodiment, doped carbon nanotubes comprise about 5 weight percent boron. In other embodiments, doped carbon nanotubes comprise nitrogen in an amount ranging from about 0.01 weight percent to about weight 30 percent or from about 5 weight percent to about 25 weight percent. In another embodiment, doped carbon nanotubes comprise nitrogen in an amount greater than 30 weight percent. In another embodiment, doped carbon nanotubes comprise from about 10 weight percent to about 20 weight percent nitrogen. In a further embodiment, doped carbon nanotubes comprise less than about 1 weight percent nitrogen.

As provided herein, carbon nanotubes can be doped with boron and nitrogen. In some embodiments, carbon nanotubes can have any weight percent or boron and nitrogen as described herein. In one embodiment, for example, doped carbon nanotubes comprise between about 5 weight percent and about 10 weight percent boron and/or nitrogen.

In some embodiments, carbon nanotubes comprise transition metals, including iron, cobalt, nickel, or combinations thereof. In one embodiment, a carbon nanotube comprises at least 0.01 weight percent of a transition metal. In another embodiment, a carbon nanotube comprises a transition metal in an amount ranging from about 0.5 weight percent to about 3 weight percent or from about 1 weight percent to about 2 weight percent.

In some embodiments of carbon nanotubes comprising iron, the iron can comprise one or more particles disposed in a cavity formed by the nanotube. In one embodiment, an iron particle can be disposed in the central cavity of a carbon nanotube. A plurality of iron particles, according to some embodiments, can be disposed in the central cavity of a carbon nanotube at regular intervals, such as 100 nm intervals. In other embodiments, iron particles can be disposed between the walls of a multi-walled carbon nanotube or throughout the branches of a branched carbon nanotube.

Alternatively, in another embodiment, an iron particle may be disposed on an outer surface of a carbon nanotube. In a further embodiment, one or more iron particles may be incorporated into the lattice of a carbon nanotube.

Iron particles, according to embodiments of the present invention, can range from a single iron atom to a cluster comprising a plurality of iron atoms. In some embodiments, iron clusters can have diameters ranging from about 2 nm to about 50 nm.

Figure 2:
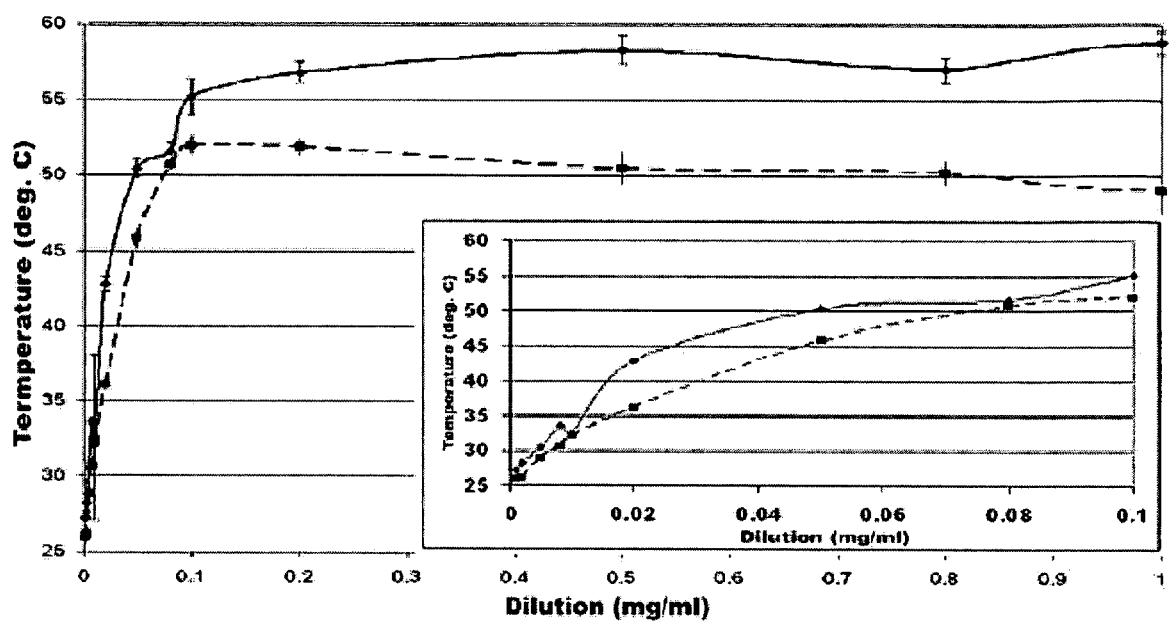
FIG. 2 illustrates thermal induction properties of MWNT as a function concentration and method of fabrication.

The amount of iron used to produce carbon nanotubes, according to some embodiments of the present invention, can effect the thermal induction properties of the carbon nanotubes. FIG. 2 illustrates the thermal induction properties of MWNT as a function of nanotube fabrication and concentration. As illustrated in FIG. 2, MWNTs produced with 60 mg iron catalyst demonstrated more efficient heating properties at each concentration in comparison with MWNTs produced with a 400 mg of iron catalyst. As a result, MWNTs thermal induction properties can be tuned through the amount of iron catalyst used to produce the MWNTs.

Moreover, in some embodiments, carbon nanotubes having any of the constructions provided herein comprise substantially no iron. In another embodiment, carbon nanotubes do not comprise iron.

In another embodiment, a nanoparticle comprises an inorganic nanoparticle. In some embodiments, inorganic nanoparticles comprise nanoshells, nanowires, nanotubes, or mixtures thereof. Inorganic nanoparticles, in some embodiments, comprise metals, including transition metals, noble metals, alkali metals, and alkaline-earth metals. Inorganic nanoparticles, in other embodiments, comprise metal oxides such as tungsten oxide ($WO_x$), vanadium oxide ($VO_x$), titanium oxide ($TiO_x$), or combinations thereof. In a further embodiment, inorganic nanoparticles comprise semiconductor materials, including II/VI and III/V semiconductors.

In one embodiment, an inorganic nanoparticle comprises a nanotube. Inorganic nanotubes, in some embodiments, have a length ranging from about 100 nm to about 3 μm or from about 400 nm to about 1500 nm. In another embodiment, inorganic nanotubes have a length ranging from about 500 nm to about 1200 nm, from about 550 nm to about 700 nm, or from about 100 nm to about 350 nm. In a further embodiment, inorganic nanotubes have a length ranging from about 700 nm to about 1 μm. In some embodiments, inorganic nanotubes have a length greater than 1 μm or a length ranging from about 1 μm to about 2 μm. In some embodiments, inorganic nanotubes have a length ranging from about 1.5 μm to about 2 μm of from about 2 μm to about 2.5 μm. In one embodiment, inorganic nanotubes have a length ranging from about 2.5 μm to about 3 μm or greater than about 3 μm.

In addition to length, inorganic nanotubes, in some embodiments, have an internal diameter ranging from about 0.1 nm to about 100 nm. In other embodiments, inorganic nanotubes have a diameter ranging from about 5 nm to about 75 nm or from about 15 nm to about 60 nm. In a further embodiment, inorganic nanotubes have a diameter ranging from about 30 nm to about 50 nm.

In one embodiment, an inorganic nanotube comprises tungsten oxide. In another embodiment, an inorganic nanotube comprises vanadium oxide or titanium oxide. In a further embodiment, an inorganic nanotube comprises boron nitride.

In some embodiments, surfaces of nanoparticles are functionalized. In one embodiment, for example, a surface of a carbon nanotube is functionalized with at least one hydrophilic chemical species. Hydrophilic chemical species suitable for functionalizing surfaces of carbon nanotubes and/or other nanoparticles described herein, in some embodiments, comprise species having carboxyl groups. In other embodiments, suitable hydrophilic chemical species comprise hydrophilic polymers such as poly(dimethyldiallylammonium chloride) (PDDA), polyethylene glycol, alkoxylated polyethylene glycol, polypropylene glycol, polyvinyl pyrrolidone, polyvinyl alcohol, polystyrene sulfonate, or poly(ε-caprolactone) or combinations thereof. In some embodiments, hydrophilic polymers comprise polyethylene oxide-propylene oxide copolymers, including block copolymers.

In some embodiments, surfaces of carbon nanotubes and/or other nanoparticles described herein are functionalized with radioactive labels, such as $^{111}$In, chelating agents, such as diethylentriaminepentaacetic acid (DTPA), and/or enzymes, such as soybean peroxidase and alpha chymotrypsin. In other embodiments, surfaces of carbon nanotubes and/or other nanoparticles are functionalized with ammonium, bovine serum albumin, schizophyllan, congo red dye, amylopectin, galactose, chitosan, or combinations thereof. In a further embodiment, surfaces of carbon nanotubes are and/or other nanoparticles described herein are functionalized with DNA, such as ssDNA, amino acids, dextran, other carbohydrates, or combinations thereof.

In some embodiments, surfaces of nanoparticles, including carbon nanotubes, are functionalized by covalently linking a hydrophilic chemical species to the surface. In other embodiments, surfaces of nanoparticles are functionalized by forming non-covalent intermolecular interactions with a hydrophilic chemical species, including ionic, dipole-dipole, and/or Van der Waals interactions. In a further embodiment, a surface of nanoparticles described herein is functionalized by forming covalent and non-covalent interactions with one or more hydrophilic chemical species.

In some embodiments, hydrophilic chemical species, including hydrophilic polymers, for nanoparticle functionalization form a plurality of interactions with a surface of the nanoparticle. In some embodiments, a hydrophilic chemical species can associate with a nanoparticle surface through a plurality of electrostatic interactions, covalent bones, dipole-dipole interactions or combinations thereof. As a result, hydrophilic chemical species, in some embodiments, do not bind to a nanoparticle surface in a 1:1 relationship. In one embodiment, for example, a single hydrophilic polymer molecule can form a plurality of ionic interactions with the surface of a nanoparticle.

Functionalization of nanoparticle surfaces with hydrophilic chemical species can increase the solubility and dispersion of the nanoparticle in polar media. Polar solutions, in some embodiments, can comprise aqueous based solutions such as saline solutions or buffer solutions. Polar matrices, in some embodiments, can comprise polymeric gels.

FIG. 1 illustrates a method of functionalizing a surface of a carbon nanotube with hydrophilic chemical species according to an embodiment of the present invention. The first step in FIG. 1 illustrates functionalization of a carbon nanotube surface by covalently linking a chemical species comprising a carboxyl group to the surface. Covalent linking of a chemical species can be accomplished by acid treatment of the nanotubes followed by 2+2 cycloadditions of the desired groups. The second step of FIG. 1 illustrates electrostatic association of a hydrophilic polymer to the surface of the nanotube through interaction with the carboxyl surface species. As illustrated in FIG. 1, the hydrophilic polymer associates with the nanotube surface through a plurality of electrostatic interactions and is not bound by a single electrostatic interaction.

In other embodiments, a surface of at least one nanoparticle is functionalized with at least one targeting ligand. In some embodiments, targeting ligands comprise polyclonal antibodies, monoclonal antibodies, chimeric antibodies, humanized antibodies, recombinant antibodies, bispecific antibodies, antibody fragments, recombinant single chain antibody fragments, aptamers, ssDNA fragments, and peptides.

Targeting ligands, according to some embodiments of the present invention, comprise chemokine and cytokine receptors such as CXCR4, CCR7, RANK, Interleukin 1 alpha, Interleukin 1 beta, and Interleukin 2-18; death receptors such as TNF, DR1-5, TRAIL, Fas, and lymphotoxin; glucose transporters (Glut1, etc.), Dmt 1, and lipocalin; viral receptors such as HSV receptor, Adenovirus receptor, stomach virus receptor, and EBV receptor; cell surface receptor ligands such as Fas ligand and Wnt; shed receptors and other proteins present in blood such as IGF (insulin-like growth factor), BMP (bone morphogenetic protein) antagonists, CA125, tissue factor, tissue plasminogen activator, thryoglobulin, alpha fetoprotein, HCG, H kininogen, L kininogen, and ferritin; cell surface receptors such as DCC (deleted in colorectal cancer), angiotensin receptors, PTCH (human homolog of Drosophila patched), RET, Kit, NGF (nerve growth factor) receptor, CGSF, GM-CSF (granulocyte macrophage colony stimulating factor) receptor, transferrin receptor, Frizzled, LRP, and Wise; cell adhesion molecules such as cadherins, CD31 (endothelial cell adhesion molecule), N-CAM (neural cell adhesion molecule), I-CAM (intercellular cell adhesion molecule), integrins, and selectins (E-selectin, P-selectin, L-selectin); receptors for extracellular matrix proteins, such as laminin receptors and fibronectin receptors; growth factor receptors such as FGF, EGF, PDGF, VEGF, FLIT, insulin receptor, IGF, BMP, met (HGF receptor), TGFbeta, and BMP antagonists; cell surface antigens such as CD5, CD44, CD20, CD57, MUC, proteoglycans, PSMA, HER2, and CEA; efflux pumps such as Mdr, Mrp, and Bcrp; and other surface proteins such as uPAR, thrombospondin, MHC molecules, Beta 2 microglobulin, Toll receptors, a LDL receptor; and/r the folate receptor.

Targeting ligands, according to some embodiments, are operable to bind to a cancer marker. In such embodiments, a targeting ligand can be designed to target a specific cancer cell marker or markers. The particular cancer cell marker may be specific to, but not limited to, the type and location of the cancer, such as, for example, tumors, metastatic cancer, minimal residual disease and the like.

The cancer marker or markers may be selected such that they represent a viable target on the cancer cell of interest, such as colorectal cancer, bladder cancer, breast cancer, endometrial cancer, kidney cancer, leukemia, lung cancer, melanoma, sarcoma, non-Hodgkin's lymphoma, pancreatic cancer, prostate cancer, skin (non-melanoma) cancer, and thyroid cancer. Cancer markers, in some embodiments, may be expressed on the surface of cancer cells and not expressed on the surface of healthy cells to permit adequate cellular differentiation. In some embodiments, cancer markers are not readily shed from cellular surfaces. In the event that a cancer marker is shed, according to some embodiments, a targeting ligand may still recognize a particular epitope of the marker that remains on the cellular surface. Alternatively, if a cancer marker is shed, the surface of a nanotube may comprise one or more additional targeting ligands operable to recognize such shed entities as markers for the cancerous cell.

In addition to at least one nanoparticle, compositions of the present invention also comprise at least one chemotherapeutic agent. Chemotherapeutic agents, according to embodiments of the present invention, can be selected according to the type of cancer being treated. Compositions of the present invention, in some embodiments, can be used in the treatment of colorectal cancer, bladder cancer, breast cancer, endometrial cancer, kidney cancer, leukemia, lung cancer, melanoma, non-Hodgkin's lymphoma, pancreatic cancer, prostate cancer, skin (non-melanoma) cancer, thyroid cancer, or combinations thereof.

In one embodiment, a chemotherapeutic agent comprises oxaliplatin, commercially available from Sanofi Aventis of Paris, France under the tradename ELOXATIN®. In another embodiment, a chemotherapeutic agent comprises Mitomycin C. In some embodiments, chemotherapeutic agents comprise alkylating agents including, but not limited to, chlorambucil, chlormethine, cyclophosphamide, ifosfamide, melphalan, carmustine, fotemustine, lomustine, streptozocin, carboplatin, cisplatin, BBR3464, busulfan, dacarbazine, mechlorethamine, procarbazine, temozolomide, thioTPA, uramustine, or combinations thereof. In other embodiments, chemotherapeutic agents comprise antimetabolites including, but not limited to, aminopterin, methotrexate, pemetrexed, raltitrexed, cladribine, clofarabine, fludarabine, mercaptopurine, thioguanine, capecitabine, cytarabine, fluorouracile, gemcitabine, or combinations thereof.

In some embodiments, chemotherapeutic agents comprise plant alkaloids including, but not limited to, docetaxel, paclitaxel, vinblastine, vincristine, vindesine, vinorelbine, or combinations thereof. In another embodiment, chemotherapeutic agents comprise cytotoxic/antitumor antibiotics, including, but not limited to, daunorubicin, doxorubicin, epirubicin, idarubicin, mitoxantrone, valrubicin, bleomycin, hydroxyurea, mitomycin, or combinations thereof. Chemotherapeutic agents, in some embodiments, comprise topoisomerase inhibitors including, but not limited to, topotecan, irinotecan, etoposide, teniposide, or combinations thereof.

In a further embodiment, chemotherapeutic agents comprise kinase inhibitors including, but not limited to, dasatinib, erlotinib, gefitinib, imatinib, lapatinib, nilotinib, sorafenib, sunitinib, vandetanib, or combinations thereof.

In some embodiments, a composition of the present invention further comprises a physiologically acceptable carrier. Physiologically acceptable carriers, according to some embodiments, comprise solutions or gels compatible with human and/or animal tissue. In some embodiments, physiologically acceptable solutions comprise water, saline solutions and buffer solutions. Buffer solutions, in some embodiments, comprise carbonates, phosphates (e.g. phosphate buffered saline), acetates, and organic buffers such as tris (hydroxymethyl)aminoethane (Tris), N-2-hydroxyethylpiperazine-N'-2-ethanesulfonic acid (HEPES), and 3-(N-morpholino)propanesulfonic acid (MOPS). In some embodiments, gels comprise hydrogels, such as those constructed from polyvinyl alcohol or dextran, such as carboxymethyl dextran. In other embodiments, gels comprise hyaluronic acid.

In some embodiments, a physiologically acceptable carrier comprises ethylene oxide and propylene oxide copolymers such as those available from BASF of Florham Park, N.J. under the tradename PLURONIC®. In other embodiments, a physiological acceptable carrier comprises collagen, chitosan, alginates, or combinations thereof. Moreover, physiologically acceptable carriers, in some embodiments, comprise dispersants such as poly(diallyldimethylammonium chloride) (PDDA), surfactants, or combinations thereof. In a further embodiment, a physiologically acceptable carrier comprises poly(lactic)-co-glycolic acid, fibrinogin, chondroitan, or combinations thereof.

Nanoparticles and chemotherapeutic agents, in some embodiments of compositions of the present invention, are dispersed throughout a physiological carrier. In one embodiment, a mixture comprises a plurality of nanoparticles and at least one chemotherapeutic agent dispersed throughout the physiological carrier wherein the chemotherapeutic agent is not disposed in the nanoparticle. In some embodiments, a mixture comprising MWNTs and oxaliplatin or Mitomycin C are dispersed throughout a physiological carrier wherein the oxaliplatin or Mitomycin C is not disposed in the MWNTs.

In another embodiment, nanoparticles having at least one chemotherapuetic agent at least partially disposed therein are dispersed throughout a physiological carrier. In one embodiment, for example, MWNTs having oxaliplatin or Mitomycin C at least partially disposed within the MWNTs are dispersed throughout a physiological carrier.

In some embodiments wherein at least one chemotherapeutic agent is disposed in a carbon nanotube, such as a SWNT or a MWNT, the carbon nanotube is capped with one or more polymeric species to trap the at least one chemotherapeutic in the nanotube. In one embodiment, a carbon nanotube having a chemotherapeutic agent at least partially disposed therein is capped with alginate. In some embodiments, the alginate is crosslinked. In another embodiment, a carbon nanotube having a chemotherapeutic agent at least partially disposed therein is capped with poly(decandiol) citrate (PDC), poly(lactic acid) (PLLA, PDLLA), poly-L-lactic-co-glycolic acid (PLGA) or combinations thereof. Polymeric materials suitable for capping carbon nanotubes are generally immiscible with water. In some embodiments, the chemotherapeutic is released from the carbon nanotube upon irradiation of the carbon nanotube as provided herein.

Compositions, according to embodiments of the present invention, comprise nanoparticles and chemotherapeutic agents in therapeutically effective amounts. In one embodiment, compositions of the present invention comprise nanoparticles at a concentration ranging from about 1 ug of nanoparticles per ml of composition (µg/ml) to about 100 µg/ml of nanoparticles. In another embodiment, compositions of the present invention comprise nanoparticles at a concentration ranging from about 10 µg/ml to about 75 µg/ml or from about 20 µg/ml to about 60 µg/ml. In some embodiments, compositions of the present invention comprise nanoparticles at a concentration ranging from about 15 µg/ml to about 50 µg/ml. In a further embodiment, compositions of the present invention comprise nanoparticles at a concentration greater than about 100 µg/ml. In some embodiments, compositions of the present invention comprise nanoparticles at a concentration less than about 1 µg/ml. In one embodiment, compositions of the present invention comprise nanoparticles at a concentration ranging from about 10 ng/ml to about 500 ng/ml or from about 550 ng/ml to about 800 ng/ml.

Moreover, in some embodiments, a composition of the present invention comprises at least one chemotherapeutic agent at a concentration ranging from about 1 µM to about 300 µM or from about 10 µM to about 250 µm. A composition, in other embodiments, comprises at least one chemotherapeutic agent at a concentration ranging from about 50 µM to about 200 µM or from about 75 µM to about 150 µM. In one embodiment, a composition of the present invention comprises at least one chemotherapeutic agent at a concentration ranging from about 90 µM to about 100 µM, from about 10 µM to about 30 µM, or from about 40 µM to about 120 µM. In a further embodiment, a composition of the present invention comprises at least one chemotherapeutic agent at a concentration greater than about 300 µM.

In another aspect, the present invention provides methods of producing compositions for the treatment of cancer as well as methods of using such compositions in the treatment of cancer.

In one embodiment, a method of producing a composition for the treatment of cancer comprises providing at least one nanoparticle, providing at least one chemotherapeutic, and mixing the at least one nanoparticle and the at least one chemotherapeutic agent. In some embodiments, the at least one nanoparticle and at least one chemotherapeutic agent are mixed in a physiologically acceptable carrier.

In another embodiment, a method for producing a composition comprises providing at least one nanoparticle, providing at least one chemotherapeutic agent, and at least partially disposing the at least one chemotherapeutic agent in the nanoparticle. In some embodiments, the at least one chemotherapeutic agent is fully disposed in the nanoparticle.

In another embodiment, a method of treating cancer comprises providing a composition comprising at least one chemotherapeutic agent and at least one nanoparticle, disposing the composition in contact with cancerous tissue, and accelerating the uptake of the at least one chemotherapeutic agent by the cancerous tissue, wherein accelerating the uptake comprises heating the cancerous tissue with the at least one nanoparticle. In some embodiments, the chemotherapeutic agent is at least partially disposed in the nanoparticle. In other embodiments, the chemotherapeutic agent is fully disposed within the nanoparticle. In a further embodiment, the chemotherapeutic agent is mixed with the nanoparticle. In some embodiments, at least one nanoparticle comprises a plurality of nanoparticles. Additionally, at least one chemotherapeutic agent comprises a plurality of chemotherapeutic agents.

In some embodiments, disposing the composition in contact with cancerous tissue comprises injecting the composition in the cancerous tissue. In other embodiments, disposing the composition in contact with the cancerous tissue comprises administering the composition intravenously, intraarterially, orally, or topically. In some embodiments, the cancerous tissue is subjected to local or regional perfusion with a composition of the present invention. In one embodiment, regional perfusion with a cancer treating composition of the present invention comprises intraperitoneal perfusion.

Heating cancerous tissue with the at least one or a plurality of nanoparticles, according to some embodiments of the present invention, comprises irradiating the at least one or plurality of nanoparticles. In some embodiments, the at least one nanoparticle is irradiated with ultraviolet radiation, visible radiation, infrared radiation, or combinations thereof. In other embodiments, the at least one nanoparticle is irradiated with radio frequency radiation. In some embodiments, the at least one nanoparticle is not ablated when irradiated. In other embodiments, the at least one nanoparticle is ablated when irradiated.

In some embodiments, the cancerous tissue is heated to a temperature of at least about 39° C. by irradiating a plurality of nanoparticles. In another embodiment, the cancerous tissue is heated to a temperature of at least about 42° C. by irradiating a plurality of nanoparticles. In a further embodiment, the cancerous tissue is heated to a temperature of at least about 45° C. by irradiating a plurality of nanoparticles. In some embodiments, the cancerous tissue is heated to a temperature greater than about 45° C. or greater than about 52° C. by irradiating a plurality of nanoparticles. The cancerous tissue, in some embodiments, is heated to a temperature less than about 39° C. or to a temperature ranging from about 39° C. to about 42° C. by irradiating a plurality of nanoparticles.

In some embodiments, the at least one nanoparticle is irradiated for less than about 20 minutes. In another embodiment, the at least one nanoparticle is irradiated for less than about 15 minutes or for less than about 10 minutes. In a further embodiment, the at least one nanoparticle is irradiated for less than about 8 minutes or less than about 5 minutes. In one embodiment, the at least one nanoparticle is irradiated for less than about 3 minutes. In some embodiments, the at least one nanoparticle is irradiated for less than about 1 minute or for less than about 30 seconds. In some embodiments, the at least one nanoparticle is irradiated for less than about 15 seconds, less than about 10 seconds, or less than about 8 seconds. In a further embodiment, the at least one nanoparticle is irradiated for less than about 5 seconds.

In some embodiments, the at least one nanoparticle is irradiated in intervals, some of which are periodic. Intervals between irradiation periods, according to some embodiments of the present invention, have a duration of about 10 seconds to about 3 hours. In other embodiments, intervals between irradiation periods have a duration of about 1 minute to about 2 hours. In another embodiment, intervals have a duration of about 10 minutes to about 1 hour. In a further embodiment, intervals between irradiation periods have a duration of about 15 minutes to about 30 minutes.

In another aspect, the present invention provides a method for treating cancer comprising providing a composition comprising at least one nanoparticle having at least one chemotherapeutic agent at least partially disposed therein, disposing the composition in contact with cancerous tissue, and releasing the at least one chemotherapeutic from the at least one nanoparticle. In some embodiments, the at least one chemotherapeutic is fully disposed within the at least one nanoparticle. At least one nanoparticle, in some embodiments, comprises a plurality of nanoparticles. Moreover, in some embodiments, at least one chemotherapeutic agent comprises a plurality of chemotherapeutic agents.

In some embodiments, disposing the composition in contact cancerous tissue comprises injecting the composition in the cancerous tissue. In other embodiments, disposing the composition in contact with the cancerous tissue comprises administering the composition intravenously, orally, or topically.

Releasing at least one chemotherapeutic agent from a nanoparticle, according to some embodiments, comprises heating the nanoparticle, wherein heating comprises irradiating the nanoparticle. A nanoparticle comprising at least one chemotherapeutic, in some embodiments, is irradiated with ultraviolet radiation, visible radiation, infrared radiation, or combinations thereof. In other embodiments, a nanoparticle comprising at least one chemotherapeutic agent is irradiated with radio frequency radiation or microwave radiation. In some embodiments, the at least one nanoparticle is not ablated when irradiated. In other embodiments, the at least one nanoparticle is ablated when irradiated.

In some embodiments, the at least one nanoparticle is irradiated for less than about 20 minutes. In another embodiment, the at least one nanoparticle is irradiated for less than about 15 minutes or for less than about 10 minutes. In a further embodiment, the at least one nanoparticle is irradiated for less than about 8 minutes or less than about 5 minutes. In one embodiment, the at least one nanoparticle is irradiated for less than about 3 minutes. In some embodiments, the at least one nanoparticle is irradiated for less than about 1 minute or for less than about 30 seconds. In some embodiments, the at least one nanoparticle is irradiated for less than about 15 seconds or less than about 10 seconds.

In some embodiments, the at least one nanoparticle is irradiated in intervals, some of which are periodic. Intervals between irradiation periods, according to some embodiments of the present invention, have a duration of about 10 seconds to about 3 hours. In other embodiments, intervals between irradiation periods have a duration of about 1 minute to about 2 hours. In another embodiment, intervals have a duration of about 10 minutes to about 1 hour. In a further embodiment, intervals between irradiation periods have a duration of about 15 minutes to about 30 minutes.

Disposing chemotherapeutic agents in nanoparticles, such as carbon nanotubes, and subsequently releasing the chemotherapeutic agents from the nanoparticles when in contact with the cancerous tissue by heating the nanoparticles, reduces the exposure of healthy, non-cancerous tissues to the toxicity of the chemotherapeutic agents. As a result, damage to healthy, non-cancerous tissues and organs can be reduced without sacrificing the efficacy of the chemotherapeutic agent in killing cancerous tissue.

The following examples will serve to further illustrate the present invention without, at the same time, however, constituting any limitation thereof. On the contrary, it is to be clearly understood that resort may be had to various embodiments, modifications and equivalents thereof which, after reading the description herein, may suggest themselves to those skilled in the art without departing from the spirit of the invention.

EXAMPLE 1

Composition Comprising Nanoparticles Having Chemotherapeutics Disposed Therein

Multi-walled carbon nanotubes are synthesized by arc growth and purified. The multi-walled carbon nanotubes are sonicated in nitric and sulfuric acids over several hours to precipitate end opening of the nanotubes. The inner diameters of the multi-walled carbon nanotubes are subsequently increased by disposing the nanotubes in a high electrolyte suspension followed by agitation to separate the inner tubes of the multi-walled nanotubes. The resulting nanotubes having a larger diameter are separated from the inner tubes through column chromatography. The opened carbon nanotubes have a length of about 900 nm and an internal diameter of about 30 nm After separation, the open carbon nanotubes are disposed in deionized water at a concentration of 1 mg/ml. The open carbon nanotubes are sonicated in the deionized water for about 10 minutes to suspend the nanotubes. 5.5 mg of dry oxaliplatin is added to 1 ml of the open carbon nanotube suspension. The nanotube/oxaliplatin composition is sonicated for 20 minutes to disperse the oxaliplatin. After sonication, the nanotube/oxaliplatin composition is stirred for one month at room temperature to at least partially dispose the oxaliplatin in the open nanotubes. The nanotube/oxaliplatin composition is subsequently centrifuged to separate the carbon nanotubes from any unadhered oxaliplatin.

EXAMPLE 2

Composition Comprising Nanoparticles Having Chemotherapeutics Disposed Therein

MWNTs were grown by chemical vapor deposition (CVD) using xylene as the carbon precursor and ferrocene as a catalyst at concentrations of 60 mg or 400 mg. Hydrogen and argon gases were used to flow the xylene through a preheater at 170° C. and a furnace oven at 700° C. An injection rate of 5 ml/hour for a one hour run yielded about 200 mg of carbon nanotubes.

The MWNTs were cut and cleaned by sonication in a mixture of 90 ml of concentrated sulfuric acid and 30 ml of concentrated nitric acid for 24 hours. The length of the nanotubes was about 2 μm with a diameter of about 20-30 nm as determined by transmission electron microscopy (TEM). MWNT stock solutions were prepared by adding 1 mg of MWNT per 1 ml of 100% ethanol with sonication to enhance MWNT dispersion. The MWNT were horn sonicated at 2 second pulses for 10 minutes.

1 ml of the MWNT stock solution was deposited onto a pyrex dish and air dried to remove the ethanol. 1 ml of oxaliplatin aqueous solution (300 μM) was added to the dried MWNT film in the pyrex dish. The oxaliplatin solution was air dried to promote capillary filling of the MWNTs.

In an alternative procedure, 1 mg of MWNT were dispersed in an aqueous oxaliplatin solution without surfactant and stirred for two weeks to dispose the oxaliplatin in the MWNTs. After filling, the MWNTs containing the oxaliplatin were dried.

EXAMPLE 3

Composition Comprising Nanoparticles Mixed with Chemotherapeutic

Multi-walled carbon nanotubes were prepared according the Example 2. The multi-walled carbon nanotubes were subsequently added at 1:10 dilutions or 1:50 dilutions in a 0.1% PLUORNIC® 127 solution. Oxaliplatin (300 μM) was added to the nanotube/PLUORNIC® 127 mixture by vortex to complete the composition.

EXAMPLE 4

Inducing Cell Death with Compositions Comprising Nanoparticles and Chemotherapeutics Three (3) 48 well plates containing 20,000 RKO cells/well (human colon carcinoma) were prepared for a series of experiments measuring cell death as a function of exposure to various compositions, including compositions according to some embodiments of the present invention. The compositions added to wells of each of the plates are set forth in Tables 1-3 below.

TABLE 1

Compositions Added to RKO Cells of Plate 1 Held at 37° C.
Composition Added to RKO Cells (300 μl)

None (Control)
Water
Pluronic ® 127 and Oxaliplatin (300 μM)
Oxaliplatin (300 μM)
Aqueous Solution of Carbon Nanotubes (100 μg/ml)
Aqueous Solution of Carbon Nanotubes (100 μg/ml) and Oxaliplatin (300 μM)

TABLE 2

Compositions Added to RKO Cells of Plate 2 Heated to 42° C.
Composition Added to RKO Cells (300 μl)

None (Control)
Water
Pluronic ® 127 and Oxaliplatin (300 μM)
Oxaliplatin (300 μM)
Aqueous Solution of Carbon Nanotubes (100 μg/ml)
Aqueous Solution of Carbon Nanotubes (100 μg/ml) and Oxaliplatin (300 μM)

TABLE 3

Compositions Added to RKO Cells of Plate 3
Held at 37° C. and Lased to at least 42° C.
Composition Added to RKO Cells (300 μl)

None (Control)
Water
Pluronic ® 127 and Oxaliplatin (300 μM)
Oxaliplatin (300 μM)
Aqueous Solution of Carbon Nanotubes (100 μg/ml)
Aqueous Solution of Carbon Nanotubes (100 μg/ml) and Oxaliplatin (300 μM)

MWNTs were grown by chemical vapor deposition (CVD) using xylene as the carbon precursor and ferrocene as a catalyst at concentrations of 60 mg or 400 mg. Hydrogen and argon gases were used to flow the xylene through a preheater at 170° C. and a furnace oven at 700° C. An injection rate of 5 ml/hour for a one hour run yielded about 200 mg of carbon nanotubes.

50 mg of the MWNTs were cut and cleaned by sonication in a mixture of 90 ml of concentrated sulfuric acid and 30 ml of concentrated nitric acid for 24 hours. The length of the nanotubes was about 2 μm as determined by transmission electron microscopy (TEM). MWNT suspensions were prepared by adding 1 mg of MWNT per 1 ml of aqueous solution having 0.1% by weight Pluronic 127® surfactant. The suspensions were sonicated to enhance MWNT dispersion. MWNT suspensions were diluted with water to a concentration of 100 μg MWNT/ml.

A solution comprising oxaliplatin at a concentration of 300 μM was obtained (Ox). For compositions comprising oxaliplatin and MWNTs (MWNT+Ox), oxaliplatin was combined with the diluted aqueous MWNT suspension to produce a solution comprising 300 μM oxaliplatin and 100 μg/ml of MWNTs.

The first plate was held at 37° C. while the second plate was heated after the addition of the compositions set forth above to the wells to achieve a temperature of 42° C. for two hours. The third plate was held at 37° C. and was irradiated after addition of the compositions to the wells with a 3W infrared laser having a wavelength of 1064 nm and a spot size of 1 cm². Wells of the third plate receiving compositions comprising carbon nanotubes (MWNT) were lased for 12 seconds and achieved a temperature of at least 42° C. resulting from the lasing. Wells of the third plate receiving compositions not comprising carbon nanotubes were lased three times for 12 seconds each with at least 20 minutes of cooling between lacings. During the cooling, wells of the third plate were returned to the incubator at 37° C.

Figure 3:
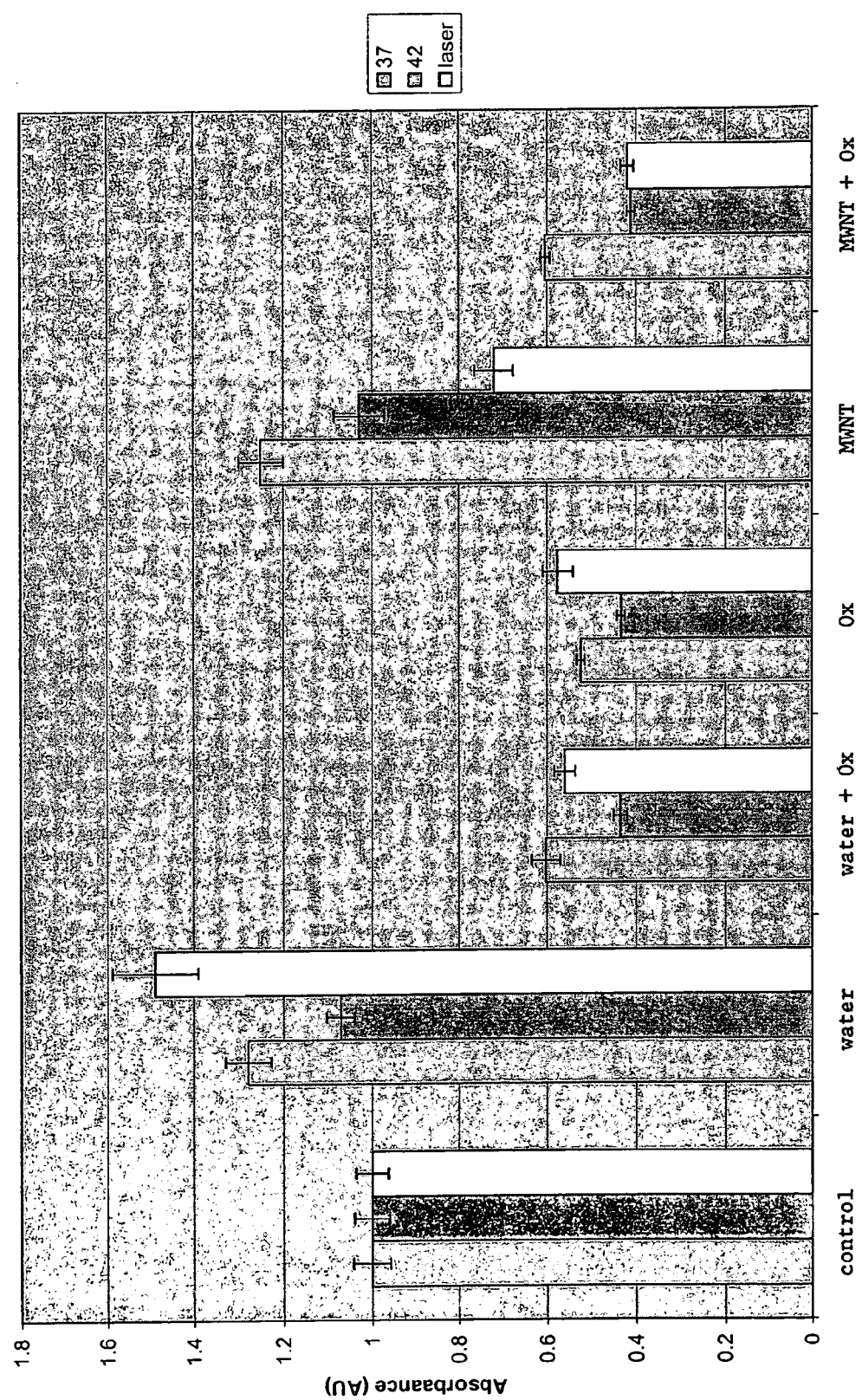
FIG. 3 illustrates assays demonstrating RKO cancerous cell-line death in view of various compositions according to one embodiment of the present invention.

Cell death resulting from the addition of the various compositions at the three temperatures was monitored by calorimetric assay. FIG. 3 illustrates the results of cell death for each of the compositions administered as a function of temperature.

As displayed in FIG. 3, no cell death resulted from the addition of water to the RKO cells in the three plates. The addition of a 0.1% Pluronic® 127 solution and the chemotherapeutic agent, oxaliplatin (Water+Ox), however, resulted in significant cell death at all three temperatures. Moreover, cell death resulting from oxaliplatin was significant for the cells heated to a temperature of 42° C. for two hours as the application of heat enhanced the uptake of the oxaliplatin.

Significant cell death was additionally demonstrated in the administration of the composition comprising carbon nanotubes and oxaliplatin (MWNT+Ox). Irradiation of this composition with infrared radiation for about 12 seconds resulted in cell death equal to or greater than that achieved by heating cells for two hours at a temperature of 42° C. in the presence of the oxaliplatin. Effectuating cancerous cell death equivalent to or greater than that achieved from heating cancer cells in the presence of oxaliplatin at 42° C. for two hours by irradiating a composition of the present invention for about 12 seconds is surprising and greatly reduces the exposure time of healthy tissues to chemotherapeutic agents. The uptake of the oxaliplatin by the cancerous cells and subsequent cell death was greatly accelerated being reduced from two hours to about 12 seconds.

EXAMPLE 5

Inducing Cell Death with Compositions Comprising Nanoparticles and Chemotherapeutics Three (3) 48 well plates containing 10,000-20,000 RKO cells/well (human colon carcinoma) and three (3) 48 well plates containing 10,000-20,000 HCT 116 cell/well (human colon carcinoma) were prepared for a series of experiments measuring cell death as a function of exposure to various compositions, including compositions according to some embodiments of the present invention. The compositions added to wells of each of the plates are set forth in Tables 4-9 below.

TABLE 4

Compositions Added to RKO Cells of Plate 1 Held at 37° C.
Composition Added to RKO Cells (300 µl)

None (Control)
Aqueous Solution of Pluronic ® 127
Aqueous Solution of Oxaliplatin (300 µM)
Aqueous Solution of Carbon Nanotubes (100 µg/ml)
Aqueous Solution of Carbon Nanotubes (100 µg/ml) and Oxaliplatin (300 µM)

TABLE 5

Compositions Added to RKO Cells of Plate 2 Heated to 42° C.
Composition Added to RKO Cells (300 µl)

None (Control)
Aqueous Solution of Pluronic ® 127
Aqueous Solution of Oxaliplatin (300 µM)
Aqueous Solution of Carbon Nanotubes (100 µg/ml)
Aqueous Solution of Carbon Nanotubes (100 µg/ml) and Oxaliplatin (300 µM)

TABLE 6

Compositions Added to RKO Cells of Plate 3
Held at 37° C. and Lased to at least 42° C.
Composition Added to RKO Cells (300 µl)

None (Control)
Aqueous Solution of Pluronic ® 127
Aqueous Solution of Oxaliplatin (300 µM)
Aqueous Solution of Carbon Nanotubes (100 µg/ml)
Aqueous Solution of Carbon Nanotubes (100 µg/ml) and Oxaliplatin (300 µM)

TABLE 7

Compositions Added to HCT 116 Cells of Plate 4 Held at 37° C.
Composition Added to HCT 116 Cells (300 µl)

None (Control)
Aqueous Solution of Pluronic ® 127
Aqueous Solution of Oxaliplatin (300 µM)
Aqueous Solution of Carbon Nanotubes (100 µg/ml)
Aqueous Solution of Carbon Nanotubes (100 µg/ml) and Oxaliplatin (300 µM)

TABLE 8

Compositions Added to HCT 116 Cells of Plate 5 Heated to 42° C.
Composition Added to HCT 116 Cells (300 µl)

None (Control)
Aqueous Solution of Pluronic ® 127
Aqueous Solution of Oxaliplatin (300 µM)
Aqueous Solution of Carbon Nanotubes (100 µg/ml)
Aqueous Solution of Carbon Nanotubes (100 µg/ml) and Oxaliplatin (300 µM)

TABLE 9

Compositions Added to HCT 116 Cells of Plate 6
Held at 37° C. and Lased to at least 42° C.
Composition Added to HCT 116 Cells (300 µl)

None (Control)
Aqueous Solution of Pluronic ® 127
Aqueous Solution of Oxaliplatin (300 µM)
Aqueous Solution of Carbon Nanotubes (100 µg/ml)
Aqueous Solution of Carbon Nanotubes (100 µg/ml) and Oxaliplatin (300 µM)

RKO and HCT 116 colorectal cancer cell lines were purchased from American Type Culture Collections (ATCC) and cultured in McCoys's media supplemented with 2.5 µg/ml of amphotericin, 1% L-glutamine, 1% penicillin/streptomycin, and 10% fetal bovine serum. Cells were seeded in wells of the appropriate trays at a density of 10,000-20,000 cells per well.

MWNTs were grown by chemical vapor deposition (CVD) using xylene as the carbon precursor and ferrocene as a catalyst at concentrations of 60 mg or 400 mg. Hydrogen and argon gases were used to flow the xylene through a preheater at 170° C. and a furnace oven at 700° C. An injection rate of 5 ml/hour for a one hour run yielded about 200 mg of carbon nanotubes.

50 mg of the MWNTs were cut and cleaned by sonication in a mixture of 90 ml of concentrated sulfuric acid and 30 ml of concentrated nitric acid for 24 hours. The length of the nanotubes was about 2 μm as determined by transmission electron microscopy (TEM).

MWNT suspensions were prepared by adding 1 mg of MWNT per 1 ml of aqueous solution having 0.1% by weight Pluronic 127® surfactant. The suspensions were sonicated to enhance MWNT dispersion. MWNT suspensions were diluted with water to a concentration of 100 μg MWNT/ml.

A solution comprising oxaliplatin at a concentration of 300 μM was obtained (Ox). For compositions comprising oxaliplatin and MWNTs (NT+Ox), oxaliplatin was combined with the diluted aqueous MWNT suspension to produce a solution comprising 300 μM oxaliplatin and 100 μg/ml of MWNTs.

As in Example 4, plate 1 of the RKO cell line was held at 37° C. while plate 2 was heated for after the addition of the compositions set forth above to the wells to achieve a temperature of 42° C. for two hours. Plate 3 was held at 37° C. and was irradiated after addition of the compositions to the wells with a 3W infrared laser having a wavelength of 1064 nm and a spot size of 1 cm². Wells of plate 3 receiving compositions comprising carbon nanotubes (MWNT) were lased three times for 8-11 seconds over a period of two hours and achieved a temperature of about 42° C. during each lasing. Wells of plate 3 receiving compositions not comprising carbon nanotubes were lased in an identical manner. After the two hour treatment period, the various treatment compositions disposed in the wells of each of plates 1-3 were replaced with media not containing nanoparticles or chemotherapeutics, and plates 1-3 were incubated at 37° C. for 48 hours.

Following incubation, the media in the wells of each of the plates was replaced with media containing MTS assay reagents from Promega's CellTiter 96® AQ$_{ueous}$ assay kit. Cell viability was quantified over a three hour period according to the manufacturers instructions.

Figure 4:
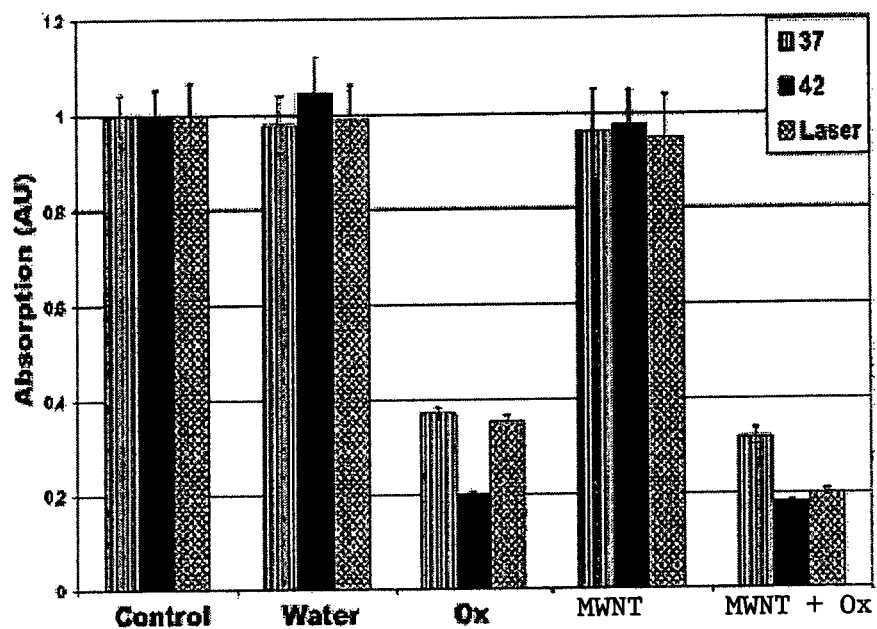
FIG. 4 illustrates assays demonstrating RKO cancerous cell-line death in view of various compositions according to one embodiment of the present invention.

As displayed in FIG. 4, no cell death resulted from the addition of the aqueous solution of Pluronic® 127 to the RKO cells in plates 1-3. Moreover, significant death resulted from the addition of oxaliplatin to the cells, including cells heated to a temperature of 42° C. in the presence of oxaliplatin.

Significant cell death was additionally demonstrated in the administration of the composition comprising MWNT and oxaliplatin (MWNT+Ox). Irradiation of this composition with infrared radiation for three 8-11 second intervals over a two hour period resulted in cell death equal to or greater than that achieved by heating cells for two hours at a temperature of 42° C. in the presence of the oxaliplatin alone. Effectuating cancerous cell death equivalent to or greater than that achieved from heating cancer cells in the presence of oxaliplatin at 42° C. for two hours by irradiating a composition of the present invention for about 8-11 seconds three times is surprising and greatly reduces the exposure time of healthy tissues to chemotherapeutic agents.

Figure 5:
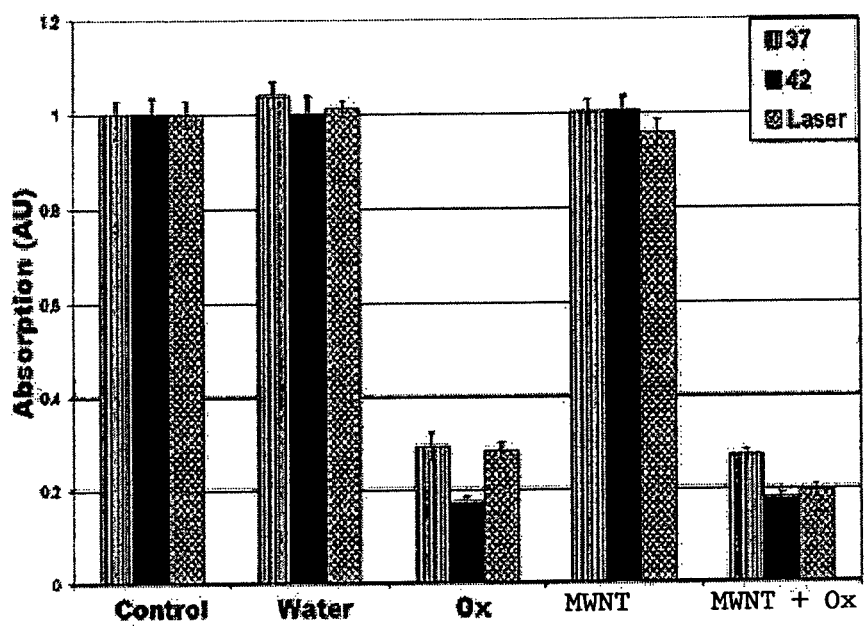
FIG. 5 illustrates assays demonstrating HCT 116 cancerous cell-line death in view of various compositions according to one embodiment of the present invention.

Moreover, plates 4-6 of the HCT 116 cell line were tested in accordance with the foregoing protocol for plates 1-3 of the RKO cell line. As illustrated in FIG. 5, the results of the HCT 116 cell line testing mirrored those of the RKO cell line.

Furthermore, as an additional viability assay, RKO cells underwent calcein/ethidium staining 48 hours post treatment. RKO cells from plates 1-3 were washed with ice cold PBS to remove adherent nanotubes and serum from the media. Solutions of calcein (2 μM) and ethidium homodimer in (4 μm) in PBS were added to the cells. Plates 1 through 3 were evaluated on an inverted Olympus fluorescent microscope in the fluorescein and rhodamine channels.

The results of the calcein/ethidium cell staining were consistent with the MTS assay results. Calcein staining of live cells demonstrated that RKO cells receiving MWNT and oxaliplatin (MWNT+Ox) followed by irradiation had a similar population to RKO cells treated with oxaliplatin at 42° C. for two hours (Ox).

EXAMPLE 6

Elemental Analysis of Cancer Cells Treated with Compositions Comprising Nanoparticles and Chemotherapeutics Oxaliplatin contains a platinum metal atom at the core of the molecule thereby permitting quantification of cellular uptake of oxaliplatin by elemental analysis of platinum.

Ten million RKO colorectal cancer cells were divided equally into three treatment groups (Group 1, Group 2, and Group 3). Each treatment group received a composition comprising 300 μM oxaliplatin and 100 μg of MWNT per ml of media. MWNTs were prepared in accordance with the procedures set forth in Example 5 herein. After receiving the MWNT-oxaliplatin compositions, Group 1 was heated to 37° C. for two hours, Group 2 was heated to 42° C. for two hours, and Group 3 was irradiated three times for 8-11 seconds over a two hour period. Each irradiation heated the RKO cells of Group 3 to 42° C.

Following the treatments, RKO cells of each group were washed with ice cold PBS and shaken on an orbital shaker in a cold room for twenty minutes to remove as much nanotube material as possible. The RKO cells were subsequently trypsinized and counted. Cell pellets were digested in 500 μl of concentrated nitric acid. Following overnight digestion at room temperature, 500 μl of ammonium hydroxide was subsequently added to neutralize the acid and water was added to bring the total volume of sample for each group to 4 ml. The amount of platinum in the cells of each group was determined and the results normalized against the number of cells in each sample.

The platinum concentration of the treated cells of Groups 1-3 was determined by Inductively Coupled Plasma (ICP) atomic emission spectrometry using a Prodigy High Dispersion ICP instrument (Teledyne Leeman Labs of Hudson, N.H.). The ICP system employed a concentric nebulizer, solution flow rate of 1.4 ml/min, and a RF power of 1.2 kW. A calibration curve was generated using 5 standards, 0 parts per billion (ppb), 300 ppb, 700 ppb, 1000 ppb, and 2000 ppb prepared by serial dilutions of a 1000 parts per million (ppm) platinum (II) chloride hexahydrate salt. A 1000 ppb spike of gold was added to all standards and samples to be used as an internal standard. The gold emission line at 242.795 nm was monitored along with the platinum emission line at 241.423 nm. Using this method, reference solutions of known platinum concentration were analyzed with greater than 99% accuracy.

Figure 6:
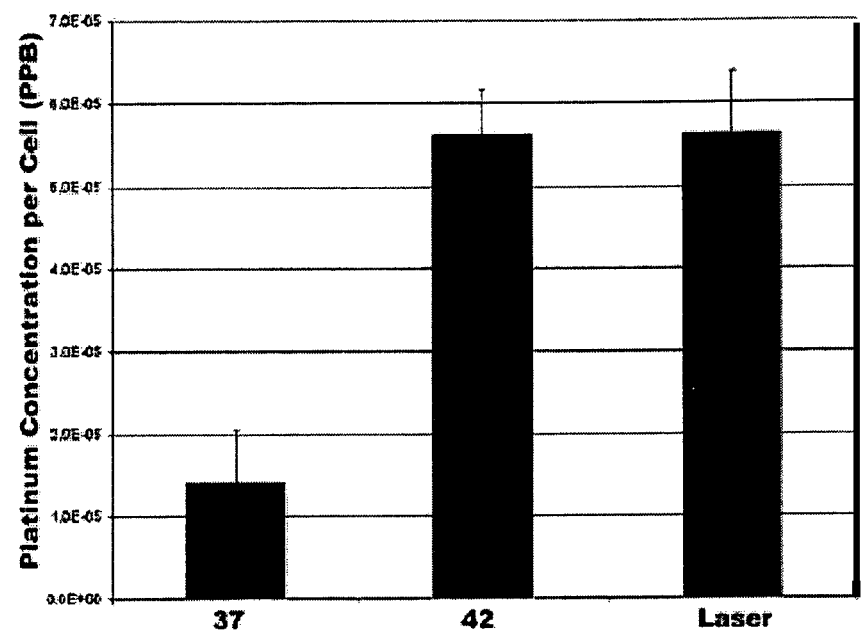
FIG. 6 illustrates the amount of platinum per RKO cell in view of a composition according to one embodiment of the present invention at various temperatures.

FIG. 6 illustrates the platinum uptake of RKO colorectal cancer cells of Groups 1-3. As illustrated in FIG. 6, RKO cells of Group 3 heated to 42° C. by brief periods of irradiation of the MWNT-oxaliplatin composition surprisingly demonstrated a platinum content similar to that of RKO cells of Group 2 being heated to 42° C. in the presence of oxaliplatin alone for 2 hours. This data is consistent with that illustrated in Examples 4 and 5 wherein cell death induced by heating cancer cells in the presence of a composition of the present invention for 8-12 seconds is substantially equivalent to cell death induced by heating cancer cells at a temperature of 42° C. for two hours in the presence of a chemotherapeutic agent.

Figure 7:
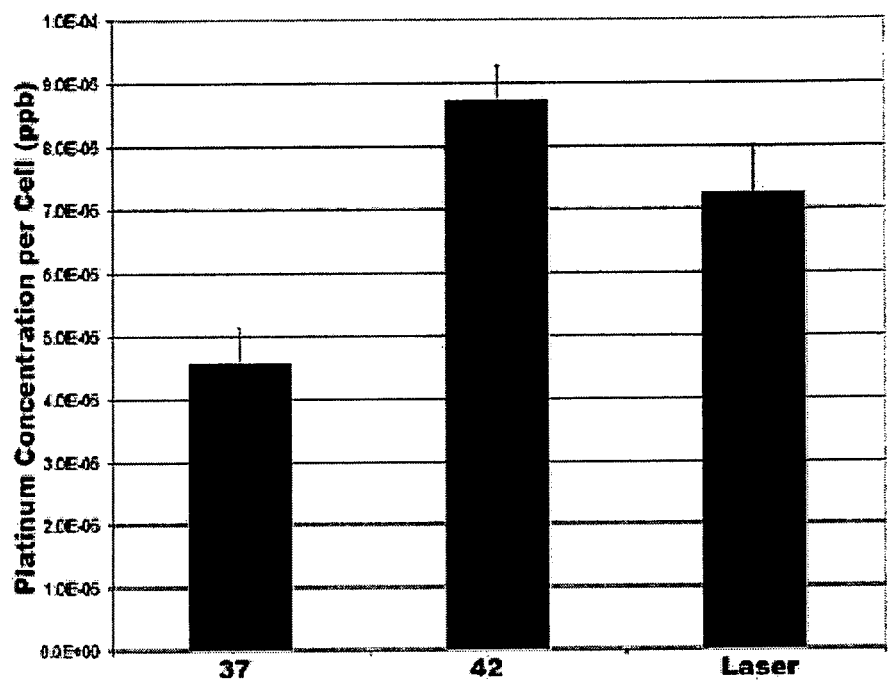
FIG. 7 illustrates the amount of platinum per HCT 116 cell in view of a composition according to one embodiment of the present invention at various temperatures.

Furthermore, 10 million HCT 116 colorectal cancer cells were divided equally into three treatment groups and underwent platinum uptake testing in accordance with the foregoing protocol set forth for the RKO colorectal cancer cells. FIG. 7 illustrates the results for the HCT 116 colorectal cancer cells. As illustrated in FIG. 7, HCT 116 colorectal cancer cells heated to 42° C. by brief periods of irradiation of the MWNT-oxaliplatin composition demonstrated a platinum content similar to that of HCT 116 cells being heated to 42° C. in the presence of oxaliplatin for 2 hours.

EXAMPLE 7

Inducing Cell Death with Compositions Comprising Nanoparticles and Chemotherapeutics Three (3) 48 well plates containing 10,000-20,000 RKO cells/well (human colon carcinoma) were prepared for a series of experiments measuring cell death as a function of exposure to various compositions, including compositions according to some embodiments of the present invention. The compositions added to wells of each of the plates are set forth in Tables 10-12 below.

TABLE 10

| Compositions Added to RKO Cells of Plate 1 Held at 37° C. Composition Added to RKO Cells (300 µl) |
| --- |
| None (Control) |
| Aqueous Solution of Pluronic ® 127 |
| Aqueous Solution of Mitomycin C (40 µM) |
| Aqueous Solution of Carbon Nanotubes (100 µg/ml) |
| Aqueous Solution of Carbon Nanotubes (100 µg/ml) and Mitomycin C (40 µM) |

TABLE 11

| Compositions Added to RKO Cells of Plate 2 Heated to 42° C. Composition Added to RKO Cells (300 µl) |
| --- |
| None (Control) |
| Aqueous Solution of Pluronic ® 127 |
| Aqueous Solution of Mitomycin C (40 µM) |
| Aqueous Solution of Carbon Nanotubes (100 µg/ml) |
| Aqueous Solution of Carbon Nanotubes (100 µg/ml) and Mitomycin C (40 µM) |

TABLE 12

| Compositions Added to RKO Cells of Plate 3 Held at 37° C. and Lased to at least 42° C. Composition Added to RKO Cells (300 µl) |
| --- |
| None (Control) |
| Aqueous Solution of Pluronic ® 127 |
| Aqueous Solution of Mitomycin C (40 µM) |
| Aqueous Solution of Carbon Nanotubes (100 µg/ml) |
| Aqueous Solution of Carbon Nanotubes (100 µg/ml) and Mitomycin C (40 µM) |

RKO colorectal cancer cell lines were purchased from American Type Culture Collections (ATCC) and cultured in McCoys's media supplemented with 2.5 µg/ml of amphotericin, 1% L-glutamine, 1% penicillin/streptomycin, and 10% fetal bovine serum. Cells were seeded in wells of the appropriate trays at a density of 10,000-20,000 cells per well.

MWNTs were grown by chemical vapor deposition (CVD) using xylene as the carbon precursor and ferrocene as a catalyst at concentrations of 60 mg or 400 mg. Hydrogen and argon gases were used to flow the xylene through a preheater at 170° C. and a furnace oven at 700° C. An injection rate of 5 ml/hour for a one hour run yielded about 200 mg of carbon nanotubes.

50 mg of the MWNTs were cut and cleaned by sonication in a mixture of 90 ml of concentrated sulfuric acid and 30 ml of concentrated nitric acid for 24 hours. The length of the nanotubes was about 2 µm as determined by transmission electron microscopy (TEM). MWNT suspensions were prepared by adding 1 mg of MWNT per 1 ml of aqueous solution comprising 0.1% by weight Pluronic 127® surfactant. The suspensions were sonicated to enhance MWNT dispersion. MWNT suspensions were diluted with water to a concentration of 100 µg MWNT/ml.

A solution comprising Mitomycin C (MMC) at a concentration of 40 µM was obtained (MMC). For compositions comprising MMC and MWNTs (MWNT+MMC), MMC was combined with the diluted aqueous MWNT suspension to produce a solution comprising 300 µM MMC and 100 µg/ml of MWNTs.

The plate 1 of the RKO cell line was held at 37° C. while plate 2 was heated after the addition of the compositions set forth above to the wells to achieve a temperature of 42° C. for two hours. Plate 3 was held at 37° C. and was irradiated after addition of the compositions to the wells with a 3W infrared laser having a wavelength of 1064 nm and a spot size of 1 cm$^2$. Wells of plate 3 receiving compositions comprising carbon nanotubes (MWNT) were lased three times for 8-11 seconds over a period of two hours and achieved a temperature of at least 42° C. during each lasing. Wells of the plate 3 receiving compositions not comprising carbon nanotubes were lased in an identical manner. After the two hour treatment period, the various treatment compositions disposed in the wells of each of plates 1-3 were replaced with media not containing nanoparticles or chemotherapetics, and plates 1-3 were incubated at 37° C. for 48 hours. Analysis of plates 1-3 was administered in accordance with the MTS assay reagents as set forth in Example 5.

Figure 8:
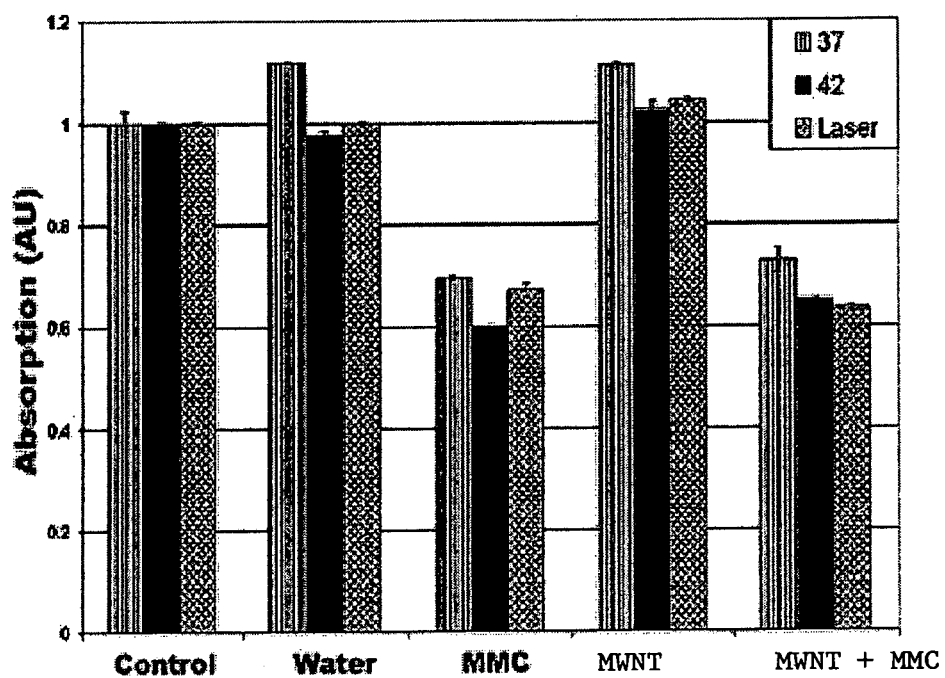
FIG. 8 illustrates assays demonstrating RKO cancerous cell-line death in view of various compositions according to one embodiment of the present invention.

As displayed in FIG. 8, significant death resulted from the addition of MMC to the cells, including cells heated to a temperature of 42° C. in the presence of MMC. Significant cell death was additionally demonstrated in the administration of the composition comprising MWNT and MMC (MWNT+MMC). Irradiation of this composition with infrared radiation for three 8-11 second intervals over a two hour period resulted in cell death similar to that achieved by heating cells for two hours at a temperature of 42° C. in the presence of the MMC. As a result, the uptake of the MMC by the cancerous cells and subsequent cell death was greatly accelerated. Effectuating cancerous cell death equivalent to or greater than that achieved from heating cancer cells in the presence of MMC at 42° C. for two hours by irradiating a composition of the present invention for about 8-11 seconds three times is surprising and greatly reduces the exposure time of healthy tissues to chemotherapeutic agents.

EXAMPLE 8

Inducing Cell Death with Compositions Comprising Nanoparticles and Chemotherapeutics Two (2) 48 well plates containing 10,000-20,000 HCT 116 cells/well (human colon carcinoma) were prepared for a series of experiments measuring cell death as a function of exposure to various compositions, including compositions according to some embodiments of the present invention. The compositions added to wells of each of the plates are set forth in Tables 13 and 14 below.

TABLE 13

Compositions Added to HCT 116 Cells of Plate 1 Heated to 42° C.
Composition Added to HCT 116 Cells (300 μl)

None (Control)
Aqueous Solution of Pluronic ® 127
Aqueous Solution of Oxaliplatin (300 μM)
Aqueous Solution of Carbon Nanotubes (100 μg/ml)
Aqueous Solution of Carbon Nanotubes (100 μg/ml) and Oxaliplatin (300 μM)

TABLE 14

Compositions Added to RKO Cells of Plate 2
Held at 37° C. and Lased to at least 42° C.
Composition Added to HCT 116 Cells (300 μl)

None (Control)
Aqueous Solution of Pluronic ® 127
Aqueous Solution of Oxaliplatin (300 μM)
Aqueous Solution of Carbon Nanotubes (100 μg/ml)
Aqueous Solution of Carbon Nanotubes (100 μg/ml) and Oxaliplatin (300 μM)

HCT 116 colorectal cancer cell lines were purchased from American Type Culture Collections (ATCC) and cultured in McCoys's media supplemented with 2.5 μg/ml of amphotericin, 1% L-glutamine, 1% penicillin/streptomycin, and 10% fetal bovine serum. Cells were seeded in wells of the appropriate trays at a density of 10,000-20,000 cells per well.

MWNTs were grown by chemical vapor deposition (CVD) using xylene as the carbon precursor and ferrocene as a catalyst at concentrations of 60 mg or 400 mg. Hydrogen and argon gases were used to flow the xylene through a preheater at 170° C. and a furnace oven at 700° C. An injection rate of 5 ml/hour for a one hour run yielded about 200 mg of carbon nanotubes.

50 mg of the MWNTs were cut and cleaned by sonication in a mixture of 90 ml of concentrated sulfuric acid and 30 ml of concentrated nitric acid for 24 hours. The length of the nanotubes was about 2 μm as determined by transmission electron microscopy (TEM). MWNT suspensions were prepared by adding 1 mg of MWNT per 1 ml of aqueous solution comprising 0.1% by weight Pluronic 127® surfactant. The suspensions were sonicated to enhance MWNT dispersion. MWNT suspensions were diluted with water to a concentration of 100 μg MWNT/ml.

A solution comprising oxaliplatin at a concentration of 300 μM was obtained (Ox). For compositions comprising oxaliplatin and MWNTs (MWNT+Ox), oxaliplatin was combined with the diluted aqueous MWNT suspension to produce a solution comprising 300 μM oxaliplatin and 100 μg/ml of MWNTs.

Plate 1 was heated after the addition of the compositions set forth above to the wells to achieve a temperature of 42° C. for two hours while plate 2 was held at 37° C. and irradiated after addition of the compositions to the wells with a 3W infrared laser having a wavelength of 1064 nm and a spot size of 1 cm². Wells of the plate 2 receiving compositions comprising carbon nanotubes (MWNT) were lased once for 8 seconds and achieved a temperature of about 42° C. during the lasing. Wells of plate 2 receiving compositions not comprising carbon nanotubes were lased in an identical manner. After the two hour treatment period, the various treatment compositions disposed in the wells of each of plates 1 and 2 were replaced with media not containing nanoparticles or chemotherapeutics, and plates 1 and were incubated at 37° C. for 48 hours.

Figure 9:
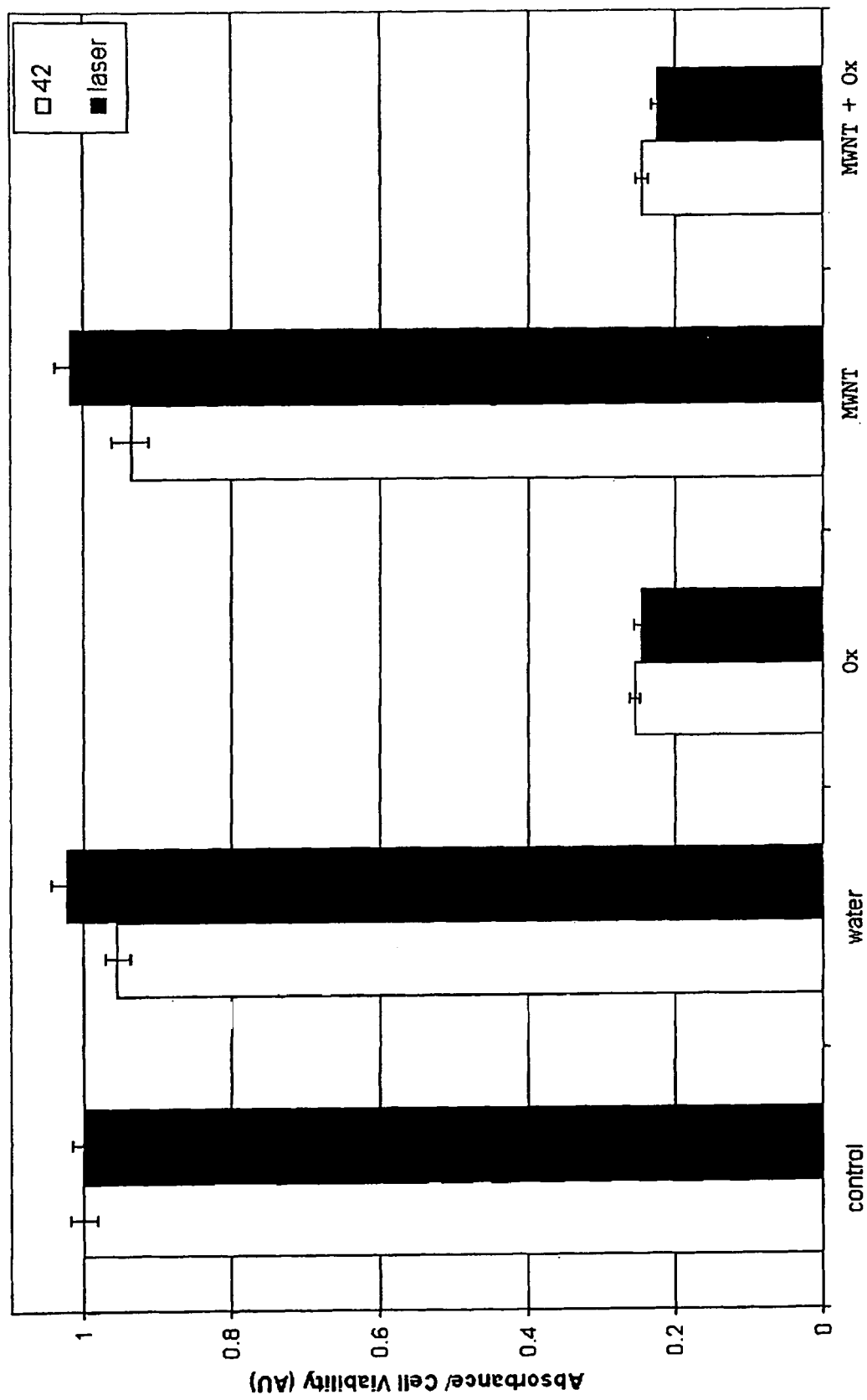
FIG. 9 illustrates assays demonstrating HCT 116 cancerous cell-line death in view of various compositions according to one embodiment of the present invention.

As displayed in FIG. 9, significant death resulted from the addition of oxaliplatin to the cells, including cells heated to a temperature of 42° C. in the presence of oxaliplatin.

Significant cell death was additionally demonstrated in the administration of the composition comprising carbon nanotubes and oxaliplatin (MWNT+Ox). Irradiation of this composition with infrared radiation for one 8 second interval resulted in cell death equal to or greater than that achieved by heating cells for two hours at a temperature of 42° C. in the presence of the oxaliplatin and MWNT. As a result, the uptake of the oxaliplatin by the cancerous cells and subsequent cell death was greatly accelerated by irradiation of a composition comprising MWNT and chemotherapeutic.

Effectuating cancerous cell death equivalent to or greater than that achieved from heating cancer cells in the presence of MMC at 42° C. for two hours by irradiating a composition of the present invention for one 8 seconds period is surprising and greatly reduces the exposure time of healthy tissues to chemotherapeutic agents.

As demonstrated in Examples 4 through 8, compositions of the present invention can limit the exposure time of healthy tissue to the inherent cytotoxicty of the chemotherapeutic agents thereby decreasing damage to and death of healthy tissues. Moreover, compositions of the present invention, in some embodiments, are applied locally or to local areas of cancer, further limiting exposure of healthy tissues to chemotherapeutic agents.

Local areas of cancer, in some embodiments, include one or a plurality of cancerous spots on or in organs such as, but not limited to, the liver, pancreas, thyroid, colon, bladder, lungs and brain. In some embodiments, compositions of the present invention are applied directly to the local spots of cancerous tissue in accordance with methods described herein. Once applied, the composition is irradiated as set forth herein to destroy the cancerous tissue. Local application of compositions of the present invention can assist in reducing the negative health effects associated with systemic administration of chemotherapeutic agents.

Local application of compositions of the present invention additionally assists in solving complications of heating large areas of tissue during hyperthermic chemotherapies, such as intraperitoneal hyperthermic chemoperfusion.

EXAMPLE 9

Compositions Comprising Nanoparticles and Chemotherapeutics in Intraperitoneal Hyperthermic Chemotherapy As provided herein, compositions of the present invention, in some embodiments, find application in hyperthermic chemotherapies. In one embodiment, compositions of the present invention comprising nanoparticles and chemotherapeutic agents are used in hyperthermic treatment of peritoneal carcitomas.

Intraperitoneal hyperthermic chemotherapy (IPHC) can be performed by open or closed abdominal techniques. A patient is cooled to a core temperature of about 34° C. to about 35° C. by passive measures (i.e., not warming airway gases or intravenous solutions) during cytoreduction. After completion of the cytoreductive surgery, peritoneal perfusion catheters are placed percutaneously. Two inflow catheters are directed beneath the left and right hemidiaphragms. One or two outflow catheters are placed in the pelvis. Drainage bulbs are attached to the end of the outflow cannulas to avoid suction injury to the bowel. Temperature probes are placed on the inflow and outflow catheters. The abdominal skin incision is temporarily closed with a running suture to prevent leakage of peritoneal perfusate. A perfusion circuit is typically established with 3L of crystalloid solution. Flow rates of about 800 to about 1000 ml/min are maintained using a roller pump managed by a perfusionist. The pelvic catheters drain to a standard cardiotomy reservoir containing a course filter to catch debris and reduce foaming. The circuit continues through a single roller pump to the patient. The temperature of the fluid in the patient-return and patient directed tubing is monitored with stainless-steel couplers with temperature probe connectors and needle probes at the tips of one inflow and one outflow cannula.

A mixture of the present invention comprising a plurality of multi-walled carbon nanotubes and one or more chemotherapuetic agents is flowed into the peritoneal cavity and in contact with the peritoneum. The abdomen is gently massaged to improve distribution of the mixture to all peritoneal surfaces. After introduction of a mixture comprising a plurality of multi-walled carbon nanotubes and at least one chemotherapeutic agent into the peritoneal cavity, the abdomen is irradiated with 1064 nm radiation. The temperature of the outflow is measured and obtains a temperature of 39° C. A target outflow temperature is 40° C.

Irradiation of the abdomen is maintained as long as needed to keep the outflow at a temperature of at least 39° C. during the perfusion. In some cases, the abdomen is irradiated in intervals to maintain an outflow temperature of at least 39° C. A maximum inflow temperature of 42.5° C. is tolerated during perfusion. The duration of the perfusion is determined by the surgeon based on a variety of factors including the extent of the cancer being treated and the identity of the chemotherapeutic being administered.

After the perfusion, the peritoneum is washed out with 2 to 3L of lactated Ringer's solution, and the peritoneum passively drained. The skin is opened, and the cannulas are removed under direct vision. The abdomen is expected, and the required anastomoses are created. The fascia and skin are then closed in standard fashion, and the requisite ostomies are created if necessary. The patient is transferred to postanesthesia care unit for aftercare and then to the intensive care unit.

EXAMPLE 10

Compositions Comprising Nanoparticles and Chemotherapeutics in Intraperitoneal Hyperthermic Chemotherapy As provided herein, compositions of the present invention, in some embodiments, find application in hyperthermic chemotherapies. In one embodiment, compositions of the present invention comprising nanoparticles and chemotherapeutic agents are used in hyperthermic treatment of peritoneal carcitomas.

Intraperitoneal hyperthermic chemotherapy (IPHC) can be performed by open or closed abdominal techniques. A patient is cooled to a core temperature of about 34° C. to about 35° C. by passive measures (i.e., not warming airway gases or intravenous solutions) during cytoreduction. After completion of the cytoreductive surgery, peritoneal perfusion catheters are placed percutaneously. Two inflow catheters are directed beneath the left and right hemidiaphragms. One or two outflow catheters are placed in the pelvis. Drainage bulbs are attached to the end of the outflow cannulas to avoid suction injury to the bowel. Temperature probes are placed on the inflow and outflow catheters. The abdominal skin incision is temporarily closed with a running suture to prevent leakage of peritoneal perfusate. A perfusion circuit is typically established with 3L of crystalloid solution. Flow rates of about 800 to about 1000 ml/min are maintained using a roller pump managed by a perfusionist. The pelvic catheters drain to a standard cardiotomy reservoir containing a course filter to catch debris and reduce foaming. The circuit continues through a single roller pump to the patient. The temperature of the fluid in the patient-return and patient directed tubing is monitored with stainless-steel couplers with temperature probe connectors and needle probes at the tips of one inflow and one outflow cannula.

A mixture of the present invention comprising a plurality of multi-walled carbon nanotubes and one or more chemotherapuetic agents is flowed into the peritoneal cavity and in contact with the peritoneum. The abdomen is gently massaged to improve distribution of the mixture to all peritoneal surfaces. After introduction of a mixture comprising a plurality of multi-walled carbon nanotubes and at least one chemotherapeutic agent, the peritoneal cavity is at least partially drained to remove excess chemotherapeutic agent. The peritoneal cavity is opened to expose localized cancerous regions on peritoneal surfaces. A continuous infrared laser (1064 nm) with a flexible fiber optic end (aperture of 1 cm in diameter) is provided to the surgeon and held at least 1 cm from an individual cancerous region on the peritoneal surface for irradiation of the cancerous region. The cancerous region has a composition comprising multi-walled carbon nanotubes and at least one chemotherapeutic agent associated with it. The cancerous region receives 10 seconds of radiation from the laser at 3W of power for a total of 30 J/cm$^2$. Exposure to the infrared laser for 10 seconds heats the cancerous region to a temperature of about 39° C. to 42° C. resulting in complete or substantially complete killing of the cancerous tissue. This process is repeated for each of a plurality of localized cancerous regions on surfaces of the peritoneal cavity. The process can be repeated until all or substantially all the cancerous regions have been completely or substantially killed.

After the localized killing of the cancerous tissue, the peritoneum is washed out with 2 to 3L of lactated Ringer's solution and closed. The fascia and skin are closed in standard fashion, and the requisite ostomies are created if necessary. The patient is transferred to postanesthesia care unit for aftercare and then to the intensive care unit.

EXAMPLE 11

In Vivo Evaluation of Localized Hyperthermia with Compositions Comprising Nanoparticles and Chemotherapeutics 15 athymic mice are divided equally into three treatment groups as provided in Table 13, with Group 1 receiving a treatment composition of 100 µg/ml of MWNTs, Group 2 receiving a treatment composition comprising 300 µM oxaliplatin, and Group 3 receiving a treatment composition comprising 300 µM oxaliplatin and 100 µg MWNT per ml.

TABLE 15

Treatment groups for in vivo evaluation

| Treatment Group | Treatment Composition |
|---|---|
| 1 | Aqueous Solution of FA Functionalized MWNT (100 µg/ml) |
| 2 | Aqueous Solution of Oxaliplatin (300 µM) |
| 3 | Aqueous Solution of FA Functionalized Carbon Nanotubes (100 µg/ml) and Oxaliplatin (300 µM) |

MWNT are produced in a manner consistent with that set forth in Example 5. Once produced, the MWNTs are functionalized with folic acid (FA) by reacting FA (Aldrich) (3.5 mM) and 5 mM 1-ethyl-3-(3-dimethylamino-propyl) carbodiimide (EDC, Fluka) with a solution of 0.35 mM PL-PEG-$NH_2$(2-distearoyl)   -sn-glycero-phosphoethanolamine-N-[amino(PEG)2000] in 10 mM phosphate buffer at a pH of about 7.5. Following dialysis to remove extra EDC and FA, the functionalized MWNTs are analyzed by spectral absorption to evaluate removal of the excess EDC and FA.

Each animal of Groups 1-3 receives intraperitoneal injections of 1E6 HeLa cervical cancer cells which express folic acid receptors. In the event the 1E6 HeLa cells are deemed inappropriate, other cancer cell lines that express folic acid receptors may be used. Two weeks after the intraperitoneal injections of the cancerous cells, the intraperitoneal cavity of each animal in Groups 1-3 is exposed, and the cancer nodules photographed allowing size and number of the nodules to be recorded.

After examination and quantification of cancer nodules, two 5 ml solutions of FA functionalized MWNTs (100 µg/ml) are provided to the intraperitoneal cavity of each animal in Groups 1 and 3. The MWNT solutions are circulated in the intraperitoneal cavity at 37° C. for 10 minutes with palpation of the abdomen to promote circulation. Following circulation, the MWNT solutions are flushed with cold saline to remove any MWNTs that have not attached to the FA receptors of the cancerous nodes. The peritoneal cavity of each animal in Groups 1 and 3 is subsequently inspected to determine the presence of MWNTs associated with the cancerous nodes.

5 ml of oxaliplatin solution (300 µM) is subsequently added to the open peritoneal cavities of each animal in Groups 2 and 3.5 ml of phosphate buffered saline is added to the open peritoneal cavity of each animal in Group 1. A continuous infrared laser (1064 nm) with a flexible fiber optic end (aperture of 1 cm in diameter) is held at least 1 cm from the open abdomen of each animal in Groups 1 and 3 and raster scanned across the surface at a power of 3W. Each area irradiated with the infrared laser receives 10 seconds of radiation at 3W of power for a total of 30 J/cm$^2$. Exposure of each area to the infrared laser for 10 seconds heats the area to a temperature of 42° C. Moreover, the peritoneal cavity of each animal in Group 2 is heated to a temperature of 42° C. for a period of two hours.

The animals of Groups 1-3 are allowed to recover for two weeks. Daily weight measurements of each animal in the study are taken to determine animal health. At the end of two weeks, the animals of each group are humanely sacrificed for histological analysis. The size and number of cancerous nodules at the time of sacrifice is compared to the initially recorded observations of size and number of cancerous nodules for each animal. Moreover, for each animal in the study, a total of about 1 to 10 mg of tumor nodule mass is retained to determine platinum content as determined by elemental analysis.

The animals of Groups 2 and 3 demonstrate a substantially similar reduction in the sizes and numbers of cancerous nodules following treatment indicating that compositions of the present invention irradiated for 10 seconds provide substantially the same result as heating cancerous tissue/cells at 42° C. in the presence of chemotherapeutic agent for two hours.

Consistent with this result, are the data returned from analyzing the platinum content of cancerous tissue taken from animals of each treatment group. Cancerous tissue from animals of Group 3 displayed substantially similar platinum content after treatment in comparison with cancerous tissue from animals of Group 2 after treatment. This indicates that compositions of the present invention irradiated for 10 seconds provide substantially the same result as heating cancerous tissue/cells at 42° C. in the presence of chemotherapeutic for two hours.

EXAMPLE 12

Compositions Comprising Nanoparticles and Chemotherapeutics in Isolated Limb Perfusion As provided herein, compositions of the present invention, in some embodiments, find application in hyperthermic chemotherapies. In one embodiment, compositions of the present invention comprising nanoparticles and chemotherapeutic agents are used in isolated limb hyperthermic perfusion.

A standard 5-Fr sheath is placed into the ipsilateral common femoral vein. A contrast hand injection usually shows the vein down to the first competent valve with contrast flowing away centrally into the iliac system. The thigh venous system is subsequently revealed to confirm the number, patency, an calibre of the superficial femoral and popliteal veins. Veins distal to the competent valves can be displayed by hand contrast injection during a Valsalva or with table tilted head up. Once in the popliteal vein, the catheter is connected to a heparinized saline infusion (1000 units heparin in 1000 ml normal saline, delivered by infusion pump) at a rate sufficient to maintain patency, generally in the order of 25 ml/h.

The arterial catheter is subsequently placed. A standard 5-Fr sheath is placed into the ipsilateral common femoral artery. Angiography is performed advancing the straight flush catheter to exclude occlusions and critical stenoses. The catheter is then connected to its own heparinized saline flush, at a rate modestly higher than the venous catheter.

Infusion of a composition comprising MWNTs and one or more chemotherapeutic agents is administered under a general anesthetic. The limb is elevated and drained of venous blood. A pneumatic tourniquet is inflated proximally to allow for effective isolation of the limb vasculature from systemic circulation. Integrity of the limb tourniquet is important to avoiding whole-body toxicity from the high concentration locally infused MWNT-chemotherapeutic composition. Additionally, toxicity of the foot is minimized by application of a compressive Esmarch bandage.

The MWNT-chemotherapeutic composition is hand injected into the arterial catheter and withdrawn from the venous catheter. Cyclical reinjection is administered over a period of 30 minutes. Total chemotherapeutic expose time is 30 minutes. Upon completion of the MWNT-chemotherapeutic composition infusion, a continuous wave infrared laser (1064 nm) with a flexible fiber optic end (aperture of 1 cm diameter) is held 1 cm from the cancerous lesions and is scanned across the surface. Each area irradiated with the infrared laser receives 10 seconds of radiation at 3W of power for a total of 30 J/cm$^2$ and reached a temperature of about 39°

C. to 42° C. Irradiation with the infrared laser in the presence of the MWNT-chemotherapeutic composition completely kills or substantially kills the cancerous lesions. The infusate is subsequently washed out with saline and he venous effluent discarded. The isolating tourniquet is deflated, and the catheters removed.

It should be understood that the foregoing relates only to preferred embodiments of the present invention and that numerous modifications or alterations may be made therein without departing from the spirit and the scope of the present invention.

That which is claimed is:

1. A method of treating cancerous tissue comprising:
   (a) providing a composition comprising a plurality of nanoparticles and at least one chemotherapeutic agent;
   (b) disposing the composition in contact with cancerous tissue, and
   (c) accelerating the uptake of the at least one chemotherapeutic agent by the cancerous tissue by irradiating the plurality of nanoparticles with electromagnetic radiation,
   wherein irradiating the plurality of nanoparticles heats the cancerous tissue to a temperature of at least about 39° C. in a time period of less than 10 seconds.

2. The method of claim 1, wherein the cancerous tissue is heated to a temperature ranging from about 39° C. to about 42° C.

3. The method of claim 1, wherein the plurality of nanoparticles comprises carbon nanotubes.

4. The method of claim 3, wherein carbon nanotubes comprise multi-walled carbon nanotubes.

5. The method of claim 3, wherein the carbon nanotubes have a length ranging from about 500 nm to about 2 μm.

6. The method of claim 1, wherein the at least one chemotherapeutic agent comprises oxaliplatin or Mitomycin C.

7. The method of claim 3, wherein the carbon nanotubes are present in the composition at a concentration ranging from about 1 μg/ml to about 100 μg/ml.

8. The method of claim 1, wherein the at least one chemotherapeutic agent is present in the composition at a concentration ranging from about 1 μM to about 300μM.

9. The method of claim 3, wherein the at least one chemotherapeutic agent is at least partially disposed within the carbon nanotubes.

10. The method of claim 1, wherein disposing the composition in contact with cancerous tissue comprises applying the composition locally to the cancerous tissue.

11. The method of claim 10, further comprising repeating steps (b) and (c) at a plurality of localized areas of the cancerous tissue.

12. The method of claim 11, wherein the plurality of localized areas are in the peritoneal cavity.

13. The method of claim 1, wherein the electromagnetic radiation comprises ultra-violet, visible, infrared radiation or combinations thereof.

14. The method of claim 1, wherein the cancerous tissue comprises colorectal cancerous tissue, bladder cancerous tissue, breast cancerous tissue, endometrial cancerous tissue, kidney cancerous tissue, lung cancerous tissue, leukemia, melanoma cancerous tissue, pancreatic cancerous tissue, prostate cancerous tissue, thyroid cancerous tissue, or combinations thereof.

15. The method of claim 1, wherein the uptake of the at least one chemotherapeutic agent by the cancerous tissue subsequent to irradiation of the plurality of nanoparticles for the 10 seconds is substantially equivalent to the uptake of the at least one chemotherapeutic agent by the cancerous tissue subsequent to heating the cancerous tissue at a temperature of 42° C. for two hours in the presence of the at least one chemotherapeutic agent alone.

16. The method of claim 1, wherein irradiating comprises providing a surgeon with a hand-held laser wherein the surgeon positions the laser proximate the cancerous tissue.

17. The method of claim 1, wherein the at least one chemotherapeutic agent is not disposed in a nanoparticle.

18. A method of treating cancerous tissue comprising:
   (a) providing a composition comprising a plurality of nanoparticles and at least one chemotherapeutic agent;
   (b) disposing the composition in contact with cancerous tissue, and
   (c) accelerating the uptake of the at least one chemotherapeutic agent by the cancerous tissue by irradiating the plurality of nanoparticles with electromagnetic radiation,
   wherein the plurality of nanoparticles comprises carbon nanotubes and irradiating the plurality of nanoparticles heats the cancerous tissue to a temperature of at least about 42° C. in a time period of less than 30 seconds.

19. The method of claim 18, wherein the carbon nanotubes comprise multi-walled carbon nanotubes.

20. The method of claim 18, wherein the carbon nanotubes have a length ranging from about 500 nm to about 2 μm.

21. The method of claim 18, wherein the carbon nanotubes are present in the composition at a concentration ranging from about 1 μg/ml to about 100 μg/ml.

22. The method of claim 18, wherein the at least one chemotherapeutic agent comprises oxaliplatin or Mitomycin C.

23. The method of claim 18, wherein the at least one chemotherapeutic agent is not disposed in a nanoparticle.

24. The method of claim 18, wherein the at least one chemotherapeutic agent is at least partially disposed within the carbon nanotubes.

25. The method of claim 24, wherein at least one carbon nanotube is capped with a polymeric material.

26. The method of claim 25, wherein the polymeric material comprises alginate, poly(lactic)-co-glycolic acid, polylactic acid, poly(decandiol) citrate, or combinations thereof.

27. The method of claim 18, wherein the cancerous tissue comprises colorectal cancerous tissue, bladder cancerous tissue, breast cancerous tissue, endometrial cancerous tissue, kidney cancerous tissue, lung cancerous tissue, leukemia, melanoma cancerous tissue, pancreatic cancerous tissue, prostate cancerous tissue, thyroid cancerous tissue, or combinations thereof.

* * * * *